(12) United States Patent
Kleine et al.

(10) Patent No.: US 9,279,776 B2
(45) Date of Patent: Mar. 8, 2016

(54) X-RAY ANALYSIS APPARATUS WITH SINGLE CRYSTAL X-RAY APERTURE AND METHOD FOR MANUFACTURING A SINGLE CRYSTAL X-RAY APERTURE

(71) Applicant: incoatec GmbH, Geesthacht (DE)

(72) Inventors: Andreas Kleine, Hamburg (DE); Josef Kreith, Leoben (AT); Frank Hertlein, Luebeck (DE)

(73) Assignee: incoatec GmbH, Geesthacht (DE)

( * ) Notice: Subject to any disclaimer, the term of this patent is extended or adjusted under 35 U.S.C. 154(b) by 182 days.

(21) Appl. No.: 13/895,389

(22) Filed: May 16, 2013

(65) Prior Publication Data

US 2013/0315375 A1      Nov. 28, 2013

(30) Foreign Application Priority Data

May 24, 2012   (DE) .......................... 10 2012 208 710

(51) Int. Cl.
  *G21K 1/02*      (2006.01)
  *G21K 1/04*      (2006.01)
  (Continued)

(52) U.S. Cl.
  CPC ........ *G01N 23/20008* (2013.01); *G02B 26/001* (2013.01); *G21K 1/02* (2013.01);
  (Continued)

(58) Field of Classification Search
  CPC .............. G01N 23/201; G01N 23/207; G01N 23/2076; G21K 1/00; G21K 1/02; G21K 1/10; G01J 3/04; G01J 3/045; G01J 3/0229; G01J 2003/1295; G02B 5/003; G02B 5/005; G02B 6/122; G02B 6/1225; G02B 26/08; G02B 27/0081; G02B 27/30; B82Y 20/00; B82Y 40/00

USPC ............... 378/70, 71, 86, 147, 148, 156–159, 378/210; 359/290, 291, 321, 351, 641, 894, 359/896; 356/310, 337, 432, 256
See application file for complete search history.

(56) References Cited

U.S. PATENT DOCUMENTS 4,393,127 A     7/1983    Greschner
5,448,073 A *   9/1995    Jeanguillaume ......... 250/363.02
(Continued)

FOREIGN PATENT DOCUMENTS

DE      4212077       10/1993
DE      10334169      2/2005
(Continued)

OTHER PUBLICATIONS

Rangelow, "Reactive Ion Etching for High Aspect Ratio Silicon Micromachining", 1997, Surface and Coatings Technology 97, Elsevier, pp. 140-150.*
(Continued)

*Primary Examiner* — Anastasia Midkiff
(74) *Attorney, Agent, or Firm* — Paul Vincent

(57) ABSTRACT

An X-ray analysis apparatus has at least one X-ray aperture (4; 4a, 4b) which delimits an X-ray beam (RS) emitted by an X-ray source (2). The at least one X-ray aperture (4; 4a, 4b) is disposed at a separation from the sample (5) and has a single crystal aperture body (8) with a through pinhole (9). The single crystal aperture body (8) forms a peripheral continuous edge (10) which delimits the X-ray beam (RS) and starting from which the pinhole (9) widens like a funnel in a direction of an outlet opening (11) of the X-ray aperture (4; 4a, 4b) in a first area (B1). The X-ray analysis apparatus reduces impairment of X-ray measurements due to parasitic scattered radiation and at little expense.

16 Claims, 16 Drawing Sheets

(51) Int. Cl.
*A61B 6/06* (2006.01)
*G01N 23/20* (2006.01)
*G02B 26/00* (2006.01)
*G02B 26/08* (2006.01)
*G02B 27/09* (2006.01)
*G01N 23/201* (2006.01)
*G01N 23/207* (2006.01)

(52) U.S. Cl.
CPC .. G21K 1/04 (2013.01); *A61B 6/06* (2013.01); *G01N 23/201* (2013.01); *G01N 23/207* (2013.01); *G02B 26/0808* (2013.01); *G02B 27/0988* (2013.01); *G21K 1/046* (2013.01)

(56) References Cited

U.S. PATENT DOCUMENTS

| | | | | |
|---|---|---|---|---|
| 6,855,945 | B1 * | 2/2005 | Silder | 250/505.1 |
| 2009/0022278 | A1 * | 1/2009 | Hugg et al. | 378/149 |
| 2012/0294426 | A1 * | 11/2012 | Panine et al. | 378/84 |
| 2013/0064354 | A1 | 3/2013 | Tache | |

FOREIGN PATENT DOCUMENTS

| | | | | |
|---|---|---|---|---|
| DE | 102007015351 | | 10/2008 | |
| JP | 2002250704 | | 9/2002 | |
| WO | WO 2011086191 | A1 * | 7/2011 | G21K 1/06 |

OTHER PUBLICATIONS

Gehrke, R. et al., "Ultrasmallangle xray scattering at the HASYLAB wiggler beamline BW4", Rev. Sci. Instrum. 66, 1354 (1995); doi: 10.1063/1.1145973.

Youli Li, "Scatterless hybrid metal-single-crystal slit for small-angle X-ray scattering and high-resolution X-ray diffraction", J. Appl. Cryst. (2008), 41, 1134-1139.

Ernest Bassous, "Fabrication of Novel Three-Dimensional Microstructures by the Anisotropic Etching of (100) and (110) Silicon", IEEE Transactions on Electron devices, vol. ED-25, No. 10, Oct. 1978.

Jan Skov Pedersen "A flux- and background-optimized version of the NanoSTAR small-angle X-ray scattering camera for solution scattering" J. Appl. Cryst. (2004), vol. 37, Pa. 369-380.

B. Kramsehpour et al., "Drilling of fine apertures in thin metallic foils using a focused ion beam", Vacuum/vol. 44/Nos. 3/4 pp. 361 to 365/1993.

Robert M. Neal et al., "Polarization phase-shifting point-diffraction interferometer", May 20, 2006/ vol. 45, No. 15/ Applied Optics.

* cited by examiner

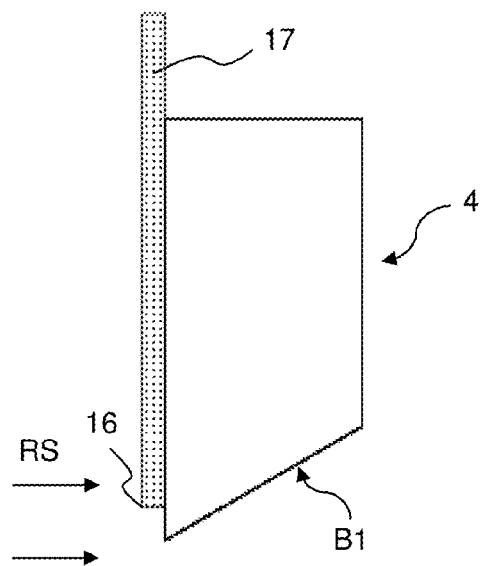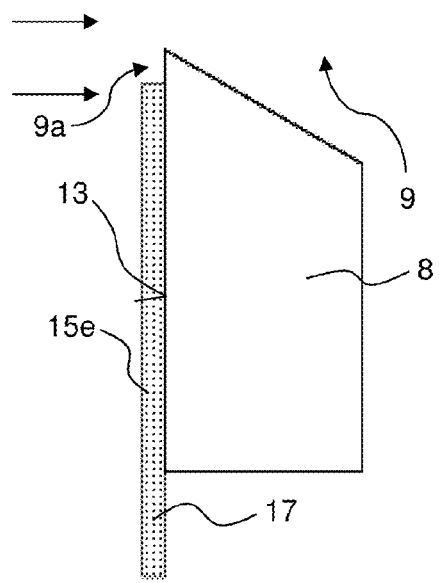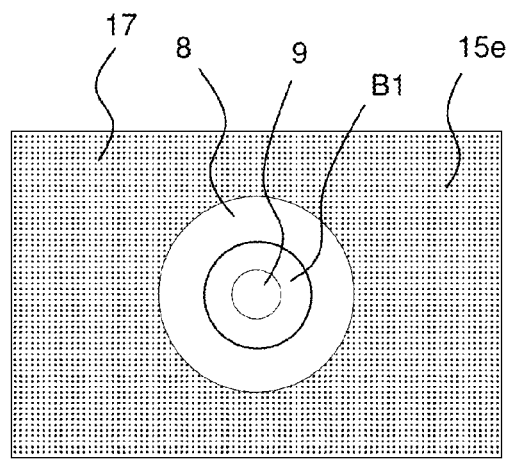
Fig. 7a          Fig. 7b

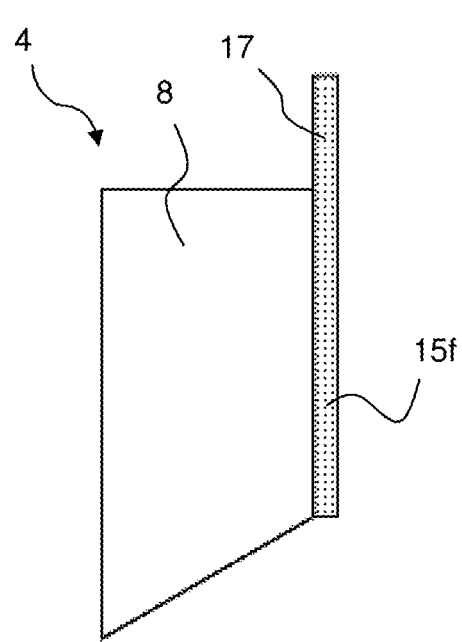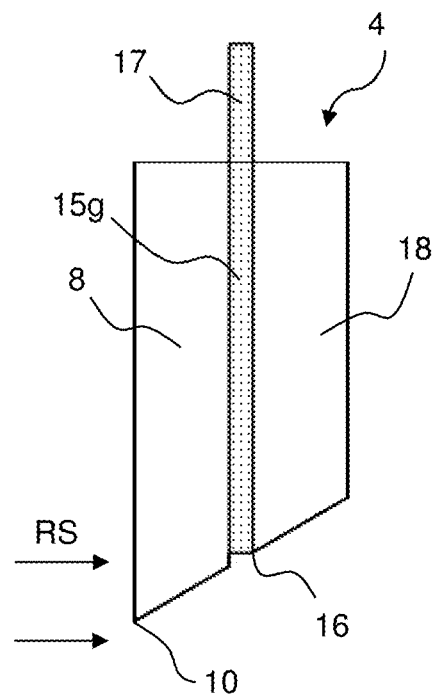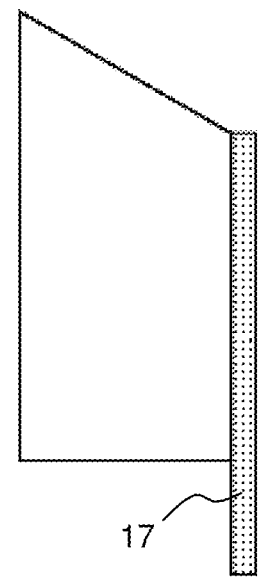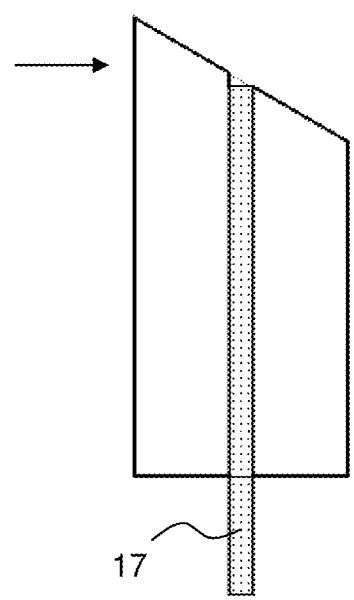
Fig. 7c　　　　　　　　　　Fig. 7d

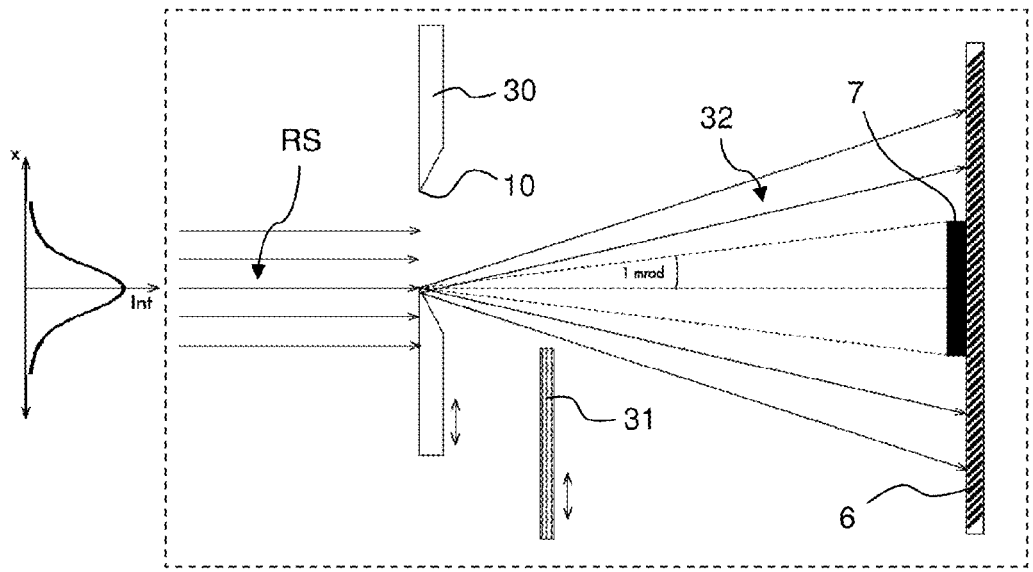
Fig. 12a
Fig. 12b
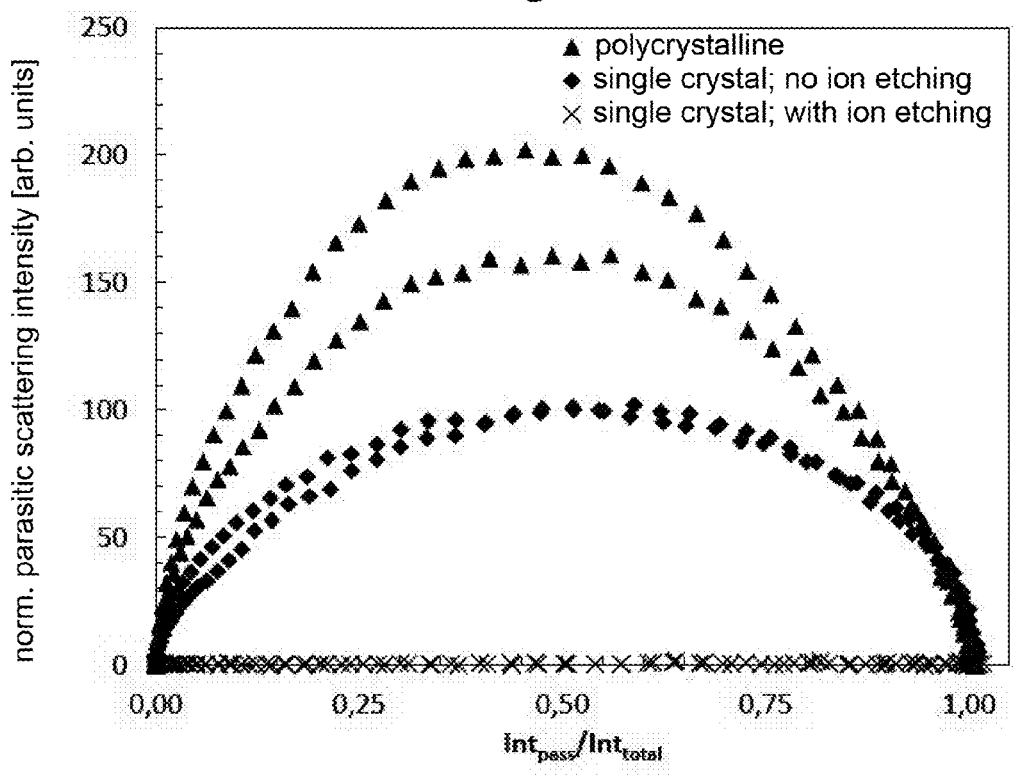

X-RAY ANALYSIS APPARATUS WITH SINGLE CRYSTAL X-RAY APERTURE AND METHOD FOR MANUFACTURING A SINGLE CRYSTAL X-RAY APERTURE

This application claims Paris convention priority of DE 10 2012 208 710.9 filed May 24, 2012 the entire disclosure of which is hereby incorporated by reference.

BACKGROUND OF THE INVENTION

The invention concerns an X-ray analysis apparatus comprising
- an X-ray source from which an X-ray beam is emitted,
- at least one X-ray aperture which delimits the X-ray beam emitted by the X-ray source,
- a sample onto which the X-ray beam, which is delimited by the at least one X-ray aperture, is directed, and
- an X-ray detector for detecting X-ray radiation emanating from the sample, wherein the at least one X-ray aperture is disposed at a separation from the sample.

An X-ray analysis apparatus of this type is disclosed by Youli Li et al., J. Appl. Cryst. (2008) 41, 1134-1139.

X-ray measurements, in particular, X-ray diffractometry and small angle X-ray scattering are used for qualitative and quantitative chemical analysis as well as for the structural analysis of samples in different fields of application.

In X-ray diffractometry, a high photon flux and high resolution are common requirements for X-ray analysis apparatus. For this purpose, the pinholes (X-ray apertures) are of decisive importance in addition to the X-ray source and the focusing or collimating X-ray optics.

The X-ray radiation that is incident on the apertures can be parasitically scattered which leads to an undesired increase in background radiation and therefore to a deterioration of the signal-to-noise ratio. In case of polycrystalline aperture material, parasitic radiation is generated on grains and grain boundaries and also by diffuse scattering on the surface roughness or total reflection at the aperture itself.

When in small angle X-ray scattering experiments, also called SAXS, an X-ray radiation wavelength $\lambda$ is used, the resolution is given by the smallest possible measurable scattering angle $\theta$ or q vector ($q=4\pi \sin(\theta)/\lambda$). This means that in SAXS experiments as small a primary beam stop as possible should be used in order to guarantee optimum resolution. With small angles, parasitic scattering at the apertures is particularly strong and results in increased measurable intensities around the primary beam stop which are superimposed on the measurement signals of the sample, which can cause reduction of the resolution or even impairment of the correct counting behavior of the detector.

SAXS measurements moreover require X-ray radiation with small divergence. Parasitic scattering at the apertures increases the divergence, which has caused the manufacturers of X-ray analysis apparatus to position three pinhole apertures each of a defined size and at defined separations one after the other in the optical path of the SAXS analysis apparatus in order to guarantee an X-ray beam with defined low divergence. The disadvantage of this design with 3 pinhole apertures consists in the massive reduction of the photon flux and accompanying considerably longer measuring times and also in the large space requirement of these measuring devices.

Single crystal diffractometry experiments, also called SCD, also utilize pinhole apertures in addition to focussing X-ray optics due to the small sample sizes, the pinhole apertures being integrated in so-called apertures. The apertures are required for delimiting the X-ray beam to the predetermined sample size. When the X-ray beam is larger than the sample, the background noise increases e.g. due to scattered radiation of the sample holder and thereby deteriorates the signal-to-noise ratio. The parasitic scattering at the pinhole apertures further deteriorates the signal-to-noise ratio. In SCD measurements, primary beam stops are used which should be selected to be as small as possible in order to only minimally delimit the q space to be examined and therefore the resolution. Due to the parasitic scattering at the pinhole apertures, a correspondingly larger primary beam stop must be used in consequence of which the resolution is correspondingly smaller. If the resolution around the primary beam is decisive, e.g. in protein crystallography, only very small pinhole apertures can be integrated when the primary beam stop size remains the same, which, in turn, greatly reduces the photon flux and correspondingly prolongs the measuring time.

In $\mu$ diffraction applications, also called $\mu$-XRD, X-ray diffraction is supposed to occur only selectively at very small surfaces or volumes of samples. Towards this end, the X-ray cross-section must be limited to a diameter of typically 10-100 $\mu$m, which also requires pinhole apertures in addition to X-ray optics. The parasitic scattering at conventional polycrystalline pinhole apertures thereby increases the surface illuminated on the sample. For this reason, the pinhole aperture size must be further reduced, which results in longer measurement times. Moreover, measurements have shown that the polycrystalline structure of the aperture becomes visible on the detector in the form of Debye-Scherrer rings, which are superimposed on the measurement signal of the sample.

Conventional X-ray apertures consist of polycrystalline metals having very good X-ray radiation absorption properties, such as tungsten, tantalum, iridium, brass, titanium, molybdenum or platinum, wherein different opening sizes and opening shapes are available. One disadvantageous property of these pinholes is the relatively strong parasitic scattering of X-ray radiation.

In Rev. Sci. Instrum. 66, 1354 (1995), Gehrke et al. have proposed an X-ray aperture for synchrotron applications which reduces parasitic scattering. The aperture comprises four motorized blades which are movably disposed opposite to each other such that a rectangular X-ray cross-sectional area is produced which can be adjusted in size. The blades consist of a material with good X-ray radiation absorption properties and their end faces comprise single crystal silicon layers. In order to prevent total reflection and therefore parasitic scattering at the end faces of the blades, the blades are tilted by a tilt angle which is larger than the angle of total reflection.

A similar principle has also been disclosed for hybrid metal single crystal blades, cf. Li et al.; Appl. Cryst. 41, 1134 (2008). Instead of tilting the blades in order to prevent total reflection, chamfered metal bases, e.g. of tungsten or brass, are used at each end face, onto each of which one rectangular single crystal substrate is glued which is polished on one side. In this fashion, the X-ray beam is mainly defined by the edges of the oppositely disposed single crystal substrates, which prevents parasitic scattering due to total reflection and also due to scattering on grain boundaries.

In document FR 2 955 391 A1, hybrid metal single crystal blades are integrated in an X-ray analysis apparatus, which is especially designed for SAXS measurements and is supposed to have a compact size in comparison with other commercially available SAXS machines.

X-ray apertures on the basis of these conventional hybrid metal single crystal blades do, in fact, enable two-dimensional beam shaping with very little parasitic scattering. However, they are difficult to produce. Manual work is constantly required. The X-ray apertures are also difficult to adjust, in particular, with respect to relative positioning of the blades. Moreover, they enable only a rectangular beam cross-section and, with respect to the resolution, at best a square beam cross-section. The minimum primary beam stop size is given by the separation between the center and the outermost point of the beam cross-sectional area. This means that a round beam cross-section permits a minimum primary beam stop size and therefore maximum resolution. In comparison therewith, the resolution of a square beam cross-section and therefore also the resolution of the systems with four hybrid blades are deteriorated by at least 41.4% (corresponds to $\sqrt{2}$).

Document JP 2002 250 704 A discloses a mask that is applied to a sample in order to select part of the sample for exposure to X-ray radiation. The mask has a funnel-shaped opening, wherein the narrower part of the opening faces the sample. The mask is produced from a single crystal material.

It is the underlying purpose of the present invention to present an X-ray analysis apparatus, in which the influence of parasitic scattered radiation on X-ray measurements is reduced with little expense.

SUMMARY OF THE INVENTION

This object is achieved by an X-ray analysis apparatus of the above-mentioned type, which is characterized in that the at least one X-ray aperture comprises a single crystal aperture body with a through pinhole, wherein the single crystal aperture body forms a circumferential continuous edge which delimits the X-ray beam and starting from which the pinhole widens in the first area like a funnel in the direction of an outlet opening of the X-ray aperture.

In accordance with the invention, the X-ray aperture is formed by a one-piece single crystal which has an pinhole through which X-ray radiation can penetrate. The pinhole has an edge through which the X-ray radiation is shadowed. The pinhole widens from the edge in the beam propagation direction, whereby a sharp (preferably atomically sharp) edge can be formed and total reflections on the X-ray aperture beyond the edge can also be prevented.

The aperture does not need movable blades, in consequence of which the aperture is easy to produce and handle. In particular, the production of apertures with single crystal aperture body for the invention can be realized by machines (and therefore in an inexpensive fashion) with high reproducibility.

Parasitic scattering is particularly low due to the single crystal aperture material. There is no scattering on grains or grain boundaries. In correspondence therewith, the signal-to-noise ratio can be improved. An inventive production method (see below) furthermore minimizes defects and roughness in the area of the edge, thereby providing an X-ray aperture (pinhole) which is practically scattering-free.

The number of pinhole apertures in a SAXS structure can be reduced to one or two within the scope of the invention. This enables higher photon fluxes and smaller primary beam stops, which again increases the resolution and reduces the measuring times. Moreover, the beam divergence can be easily adjusted through the separation of the pinhole apertures and can be reduced, if necessary. The space required for a SAXS measuring device is furthermore greatly reduced.

Within the scope of the invention, considerably smaller primary beam stops can be used for an SCD structure with identical photon flux compared with prior art, which considerably increases the resolution. When the primary beam stop size remains the same, it is possible to use larger pinhole aperture diameters, which enables higher photon fluxes and therefore shorter measuring times. The number of pinhole apertures can moreover be reduced to one or two, thereby reducing the space that is required.

Larger pinhole diameters can be used in µ-XRD measuring configurations, which results in higher photon fluxes and therefore shorter measuring times. Furthermore, Debye-Scherrer rings resulting from a polycrystalline pinhole aperture material are no longer superimposed on the signal of the sample to be measured. The single crystal aperture material only generates single diffraction reflexes on the detector. Firstly, these reflexes are superimposed on the measurement signal of the sample to a considerably smaller degree, and secondly, they can be unambiguously associated with the pinhole apertures, which facilitates evaluation of the measurement results.

The pinhole can be produced to have a shape that is adjusted to the requirements of the selected X-ray analysis experiment. The shape of the pinhole is not limited to a rectangular shape but can basically be arbitrarily selected. In particular, a circular shape can be selected to permit use of a particularly small, preferably circular primary beam stop, which improves the resolution capacity compared with a square beam cross-section in SAXS and SCD measurements by a factor of $\sqrt{2}$. The pinhole or the beam shape can, in particular, also be adjusted to the sample geometry, for example, to ensure uniform illumination of the sample.

Moreover, the scattering-free (or at least low-scattering) X-ray apertures with single crystal aperture body can be adjusted to the optical path of an X-ray analysis apparatus much faster than conventional (polycrystalline) X-ray apertures, since the reduced parasitic scattering permits larger tolerances. Relative adjustment of movable blades is not necessary since they have been omitted.

For converting an existing SAXS laboratory device, compact, scattering-free (or at least low-scattering) X-ray apertures with single crystal aperture body in accordance with the invention are clearly to be preferred in comparison with conventional blade systems, since an aperture change with the inventive X-ray apertures can be realized more quickly, more easily and with less expense, additionally guaranteeing a higher resolution.

The material of the single crystal aperture body may, in particular, be silicon or germanium. These materials are available in single crystal form with high purity at low cost. Further aperture materials may e.g. be single crystal tantalum, platinum, tungsten, lead or iridium. The latter materials have a particularly high density and therefore a larger absorption capacity. They are preferred for high-energy X-ray radiation or for X-ray radiation of high intensity. The selection of the material should include the consideration that the irradiated X-ray radiation does not excite fluorescence radiation and/or Bragg reflexes in the small angle area in the single crystal, which could contribute to a parasitic scattered signal. The aperture body may, in particular, be cut out of a wafer, e.g. a standard wafer (if available), which is preferably polished on one or two sides for reducing the surface roughness. The aperture body material may be doped. However, undoped material with a smallest possible defect density is preferably used.

The aperture thickness of the aperture body (separation between inlet opening and outlet opening in the beam direction) should be at least 0.05 mm and is preferably in a range between 0.1 mm and 3 mm.

The pinhole of the X-ray aperture has its minimum cross-sectional area in the area of the edge, which is the beam-defining cross-sectional area. The material of the aperture body is recessed to the outside in the beam direction before and after the edge transversely to the beam direction approximately in a funnel-shape or also in the form of a wall that extends perpendicularly to the beam direction. In the area of its pinhole, the X-ray aperture is typically structured to be axially symmetrical, in particular, rotationally symmetrical with respect to a symmetry axis which extends through the center of the beam-defining cross-sectional area. This simplifies production and guarantees optimum beam shaping with little parasitic scattering.

In the X-ray analysis apparatus in accordance with the invention, the overall optical path or a part thereof is preferably located in an evacuated volume at a pressure of between 10 mbar and $10^{-8}$ mbar. The overall optical path or a part thereof may also extend within protective gas, such as e.g. helium or nitrogen. Both variants reduce or prevent air scattering, which improves the signal-to-noise ratio.

In one preferred embodiment of the inventive X-ray analysis apparatus, the pinhole has a round, in particular, circular cross-section at least in the area of the edge and of the first area. In this case, it is also possible to use a round, in particular, circular primary beam stop, for which reason, a minimum primary beam stop size can be selected. This allows particularly high resolutions. A circular pinhole shape or a circular X-ray beam cross-section achieves improvement by a factor of $\sqrt{2}$ compared with a square aperture or a square beam cross-section. A diameter of the (circular) beam-defining cross-sectional area of a range between 0.001 mm and 3 mm is particularly preferred, in particular, between 0.05 and 1.5 mm. For example, rectangular aperture cross-sections can alternatively also be used.

In one particularly preferred embodiment, the edge extends in an edge plane, wherein a surface normal of the edge plane extends substantially parallel to the direction of propagation of the X-ray beam delimited by the X-ray aperture. This establishes an overall favorable scattering behavior.

In another preferred embodiment, the first area is designed like a truncated cone and has an opening angle α of between 5° and 60°, preferably between 10° and 30°, particularly preferred between 12° and 18°. These opening angles have turned out to be favorable in practice. They can be easily produced with a sufficiently large size, in particular, with the preferred materials of the aperture body (e.g. Si, Ge or Ta) with the typical X-ray wavelengths (e.g. Cu—Kα radiation) in order to avoid total reflection in the first area. The opening angle α is the angle of inclination of the lateral area of the (straight circular) truncated cone, i.e. of the perforated wall in the first area with respect to the axis (of rotational symmetry) of the (straight circular) truncated cone, which typically corresponds to the direction of propagation of the X-ray beam delimited by the X-ray aperture.

In another particularly advantageous embodiment, the pinhole widens, starting from the edge, like a funnel in a second area in the direction towards an inlet opening of the X-ray aperture. In comparison with a unilateral funnel-shaped widening, a larger amount of single crystal material is located in the direct vicinity of the edge in this case. This results in a higher absorption of the X-ray radiation incident on the aperture (and not on the pinhole).

In one preferred further development of this embodiment, the second area is designed in the shape of a truncated cone and has an opening angle β of between 20° and 80°, preferably between 25° and 70°, particularly preferred between 30° and 60°. This has again turned out to be favorable in practice, in particular, in order to facilitate production and avoid total reflections. The opening angle β is the angle of inclination of the lateral area of the (straight circular) truncated cone, i.e. of the perforated wall in the second area with respect to the axis (of rotational symmetry) of the (straight circular) truncated cone, which typically corresponds to the direction of propagation of the X-ray beam delimited by the X-ray aperture.

In one alternative embodiment, the edge is formed at a front side of the X-ray aperture such that the edge also delimits an inlet opening of the X-ray aperture. In other words, the edge is located directly at the front side of the aperture body facing the source. This embodiment is particularly easy to produce.

In one preferred embodiment, the roughness depth of the X-ray aperture in one wavelength range between 10 nm and fpm is smaller than 100 nm at least in the area of the edge. With this roughness, the parasitic scattering is particularly small. The required roughness, in the present case in the form of a roughness depth (peak-to-valley), can be obtained with the inventive production method described below (in particular, the proposed post-processing by means of ion etching). The same roughness condition typically also applies to the first area and, if necessary, to the second area.

In another preferred embodiment, the following applies to an edge sharpness of the edge of the X-ray aperture: Edge radius<5 μm. The edge radius is the radius of the largest circle that can be applied to the profile of the edge at the inside (with the area level parallel to the axis of symmetry of the pinhole or parallel to the beam direction) without intersecting the profile (see in this respect also FIG. 3c). The profile of the edge can be seen e.g. in the scanning electron microscope after corresponding preparation of the aperture body (e.g. by opening with a saw or polishing up). An edge radius<5 μm helps to keep parasitic scattering low. The required edge sharpness can also be established with the inventive production method.

In another preferred embodiment, the X-ray aperture is designed in such a fashion that, when the edge is irradiated with an approximately parallel X-ray beam with half-covered aperture, an integral scattered light portion which is measured starting from a scattering angle of 1 mrad, is smaller than $5*10^{-5}$. The required low parasitic scattering can be achieved with an X-ray aperture that is produced in accordance with the above presented production method. An aperture of this type or an associated X-ray analysis apparatus can perform X-ray measurements with particularly high resolution.

In another particularly advantageous embodiment, the single crystal aperture body is connected, in particular, glued to an absorption structure, the material of the absorption structure absorbs X-ray radiation to a greater extent than the material of the single crystal aperture body, in particular, wherein the material of the absorption structure is tungsten, tantalum or lead, and the absorption structure is recessed with respect to the edge transversely to the direction of propagation of the X-ray beam delimited by the at least one X-ray aperture. The absorption structure attenuates penetration through the aperture of X-ray radiation remote from the pinhole, solely due to the extended absorption length. The material of the absorption structure is preferably single crystalline (but need not necessarily be single crystalline). In particular, Pt, Ir, Ta, Pb, Mo, Ti, Ag and W are suitable materials. Parasitic scattering on the absorption structure is virtually not important since the single crystal aperture body projects past the absorption structure towards the pinhole at a separation (typically along the entire circumferential edge of at least 0.1 mm) that is adjusted to the X-ray source (wavelength and intensity) and therefore blocks the scattered radiation. Absorption structures are used, in particular, for high intensity of the X-ray radiation of the X-ray source or also for high energy (short wavelength) of the X-ray radiation. Absorption structures can e.g. be provided on a front wall (with respect to the beam propagation direction), a rear wall, an inner wall of a tunnel (inner side of the pinhole, wall of the funnel) and/or in a sandwich arrangement on the X-ray aperture. Absorption structures or parts thereof may be realized e.g. in the form of foils or plates with an pinhole for the X-ray beam or in the form of deposited layers on the aperture body (which has an pinhole in any event). The beam-defining cross-sectional area of the aperture is neither partially nor completely covered by an absorption structure.

In one advantageous further development of this embodiment, the absorption structure forms a holder which projects past the aperture body in a direction transverse to the propagation direction of the X-ray beam which is delimited by the at least one X-ray aperture. The holder enables easy and quick installation of the X-ray aperture in an inventive X-ray analysis apparatus. Handling or mounting during post-processing is also facilitated, if necessary. The holder may comprise e.g. threads, hooks, grooves, recesses, bulges, depressions, holes or the like for mounting the absorption structure.

In one advantageous embodiment, the single crystal aperture body is connected, in particular glued, to a cover structure, the material of the cover structure absorbs X-ray radiation to a lesser extent than the material of the aperture body, in particular, wherein the material of the cover structure is kapton or beryllium, and the cover structure covers an inlet opening and/or the outlet opening of the X-ray aperture, in particular, wherein the pinhole is closed by the cover structure in a gas-tight or vacuum-tight fashion. The cover structure protects the area of the edge from being soiled, in particular, when both sides are closed. The cover structure can additionally be used as a filter for electromagnetic radiation of certain energy fields (preferably within the energy range of 100 eV to 100 keV) in dependence on the material thereof. When the pinhole is closed in a gas-tight or vacuum-tight fashion (either on one or both sides), the X-ray aperture, as a combination component, can additionally be used as an X-ray window. In the latter case, the material of the cover structure preferably has only weak scattering and weak absorption properties in the range between 100 eV and 100 keV. Areas of different pressure are often found in X-ray analysis apparatus such that the combination component (by means of which these areas can be separated) obtains a more compact structure. For separating a vacuum, the cover structure is advantageously vacuum-tight up to $10^{-8}$ mbar. The material of the cover structure is advantageously in the form of a foil or plate, typically having a thickness in a range between 5 μm and 1 mm. The cover structure is typically arranged on the front side and/or the rear side of the X-ray aperture.

In another advantageous embodiment, the single crystal aperture body is connected, in particular glued, to a fill structure and the material of the fill structure absorbs X-ray radiation to a lesser degree than the material of the aperture body, in particular, wherein the material of the fill structure is kapton or beryllium, and the fill structure fills the pinhole. The fill structure can effectively protect the pinhole from being soiled and mechanically damaged. The material of the fill structure can also be used as an energy filter. When the fill structure simultaneously seals the pinhole in a gas-tight or vacuum-tight fashion, it can moreover turn the X-ray aperture into a combination component which can also be used as an X-ray window. Details in connection with these functions are described in the above embodiment and also apply to this embodiment.

In another preferred embodiment, the X-ray analysis apparatus comprises two X-ray apertures that are disposed at a separation from the sample and each comprising a single crystal aperture body with a through pinhole, wherein the single crystal aperture bodies each form a circumferential continuous edge that delimits the X-ray beam, and starting from which the pinhole of the respective aperture body widens like a funnel in a first area towards an outlet opening of the respective X-ray aperture. In many applications, in particular for a SAXS apparatus, exactly two X-ray apertures with single crystal aperture bodies are sufficient (instead of three conventional apertures), thereby achieving a higher photon flux and therefore shorter measurement time and a more compact construction. The parasitic scattering is moreover reduced such that a higher resolution can also be achieved. Either one or both X-ray apertures may be designed in correspondence with the above-described embodiments. Both X-ray apertures are arranged upstream of the sample (with respect to the propagation direction of the X-ray beam). The X-ray apertures typically have truncated first areas, the rotational axes of symmetry of which are on the same straight line, wherein the straight line extends parallel to the propagation direction of the X-ray beam. The separation between the two apertures can be variably adjusted. For this reason, the divergence can be adjusted and adapted to the experiment to be performed. The divergence div can be estimated through div=(d1+d2)/l12, with d1, d2: diameter of the beam-shaping cross-sectional areas of the apertures 1, 2, and l12: separation between the apertures 1, 2. When the divergence is adjusted to be small (i.e. large aperture separation l12 or small d1, d2), the size of the primary beam stop can be selected to be correspondingly small in order to obtain a higher resolution capacity.

In one embodiment of the inventive X-ray analysis apparatus, the X-ray analysis apparatus advantageously has a beam-shaping element, in particular, a Goebel mirror or Montel mirror which is disposed directly at the X-ray source. The beam-shaping element typically parallelizes or focuses the X-ray beam emitted by the source (e.g. focuses it to the sample). Additional monochromatization is also possible (if required). An X-ray aperture in accordance with the invention may, in turn, be mounted to the beam-shaping element on the outlet side. This embodiment contributes to a compact structure. It should be noted that, in accordance with the invention, a beam-shaping element can also be arranged independently of (at a separation from) the X-ray source. It is also possible to dispose an X-ray aperture in accordance with the invention on a vacuum chamber/protective gas chamber or as part of the outer boundary of a vacuum chamber/protective gas chamber or to dispose an inventive X-ray aperture as a solitary item. It is moreover also possible to integrate one or more X-ray apertures in accordance with the invention in a aperture as it is used e.g. for SCD or μ-XRD experiments and position it/them in the inventive X-ray analysis apparatus between the X-ray source and the sample or between the X-ray optics (beam-shaping element) and the sample.

In another particularly preferred embodiment, the X-ray analysis apparatus is designed as a small-angle X-ray scattering measuring arrangement or a single crystal scattering measuring arrangement, in particular, comprising a primary beam stop. For a small-angle X-ray scattering measuring arrangement (SAXS measuring arrangements) only one to two X-ray apertures with single crystal aperture bodies are required which offer the advantage of a higher photon flux, more compact structure, and higher resolution. Similar advantages also result from single crystal measuring arrangements or single crystal diffractometry measuring arrangements (also called SCD measuring arrangements; SCD=single crystal diffraction). Similar to SAXS measurements, conventional (polycrystalline) apertures in SCD applications either require a very large primary beam stop, which reduces the resolution, or very small pinhole apertures are installed in order to be able to use correspondingly small primary beam stops. In the latter case, however, the intensity of the X-ray beam is greatly reduced, which increases the measuring times. When low-scattering or scattering-free apertures with single crystal aperture bodies are used in SCD structures, the primary beam stop of a size of 1.5 mm, which is used as a standard, can be considerably reduced in size, e.g. to a diameter of 1 mm or less, which considerably improves the resolution.

In a further preferred embodiment of the inventive X-ray analysis apparatus, the X-ray analysis apparatus is designed as a µ-XRD measuring arrangement. The pinhole apertures (with single crystal aperture body) of this measuring arrangement typically have a diameter of a range between 10 µm and 100 µm. Since scattering-free or low-scattering pinhole apertures generate (almost) no parasitic scattering, larger pinhole diameters can be used compared with conventional polycrystalline apertures, which increases the photon flux and reduces the measuring time. The single crystal pinhole apertures moreover do not generate any Debye-Scherrer rings on the detector, which would be superimposed on the measurement signal, but only individual diffraction reflexes that can be unambiguously identified. This property facilitates evaluation of the measurement results.

Production method and post-processing method in accordance with the invention

The present invention also concerns a method for producing an X-ray aperture, comprising the following steps:
a) introducing a through pinhole into a single crystal aperture body, such that the single crystal aperture body forms a circumferential continuous edge for delimiting an X-ray beam, from which edge the pinhole widens like a funnel in a first area in a direction towards an outlet opening;
b) removing material from the surface of the aperture body at least in the area of the edge and of the first area through ion beam etching.

Within the scope of the inventive method, a scattering-free or at least low-scattering X-ray aperture can be produced in a simple fashion for an inventive X-ray analysis apparatus described above.

During the inventive post-processing in accordance with step b), ions, preferably argon ions, are accelerated in a vacuum, typically with an acceleration voltage in a range between 1 kV and 10 kV, and are directed with high kinetic energy onto the surface of the single crystal aperture body, in particular, in the area of the edge. The accelerated ions thereby remove material from the surface of the single crystal aperture body (e.g. surface soiling but also single crystal material of the aperture body itself). Within the scope of step b), only a small amount of material in the range of a few tens of µm (e.g. 10 µm up to 100 µm) is typically removed. In case of a circular pinhole, the diameter of the pinhole typically increases by approximately 100 µm due to post-processing in accordance with step b) (which should be taken into consideration in step a) if required). Near-surface defects which were introduced into the single crystal in the area of the pinhole or the edge within the scope of step a) are removed, thereby effectively reducing the defect density in the aperture body, which reduces parasitic scattering.

The ion etching process enables careful post-processing of the edge or its surroundings. This is particularly important since, due to the inventive design, little absorbent single crystal material is present and also since a particularly large number of photons are incident on the aperture (assuming e.g. a Gauss-shaped intensity profile of the X-ray beam) and can be parasitically scattered. Absorbates and adsorbates are moreover removed and the surface roughness is reduced. These two effects also reduce the parasitic scatting during later use in an X-ray analysis apparatus.

Within the scope of step b), the overall pinhole surface of the aperture body is preferably post-processed. If a funnel-shaped second area is provided towards the side of the inlet opening, this area is preferably also post-processed. The angle of incidence of the ions on the surface of the aperture body can advantageously be varied e.g. by tilting the ion source or the aperture body. The ion source can advantageously also be moved relative to the aperture body e.g. in order to vary the separation (for adjusting the removal rate and/or the polishing cross-section) or also for shifting the surface swept by the ion beam (e.g. when the diameter of the ion beam is not sufficient for simultaneously processing the overall relevant part of the aperture body). The ion beam is typically adjusted in such a fashion that it is aligned in parallel with the symmetry axis of the aperture (which also corresponds to the intended X-ray direction).

In one particularly preferred variant of the inventive production method, electrical discharge machining and/or cold laser ablation is used in step a) for introducing the pinhole. Within the scope of cold laser ablation, a pulsed laser operation with a pulse duration of one single laser pulse of 15 ps or less is preferably used. Both methods (electrical discharge machining and cold laser ablation) have proven to be well suitable for introducing (circular) round pinholes. The use of these methods entails introduction of only minor (in particular near-surface) defects into the single crystal aperture body. In contrast thereto, e.g. mechanical drilling has not proven to be suitable within the scope of step a), since this method also produces defects in deeper layers of the aperture body. It is also important that cold laser ablation and electrical discharge machining produce comparatively large opening angles α of the first area (approximately ≥15°) within the scope of step a), which e.g. cannot be realized or only with great difficulty with DRIE (deep reactive ion etching).

In one preferred variant, the pinhole is produced in step a) at least in the area of the edge and of the first area with a round, in particular, circular cross-section. The (circular) round cross-section remains during post-processing in step b) such that the produced X-ray aperture can then be used in an X-ray analysis apparatus with high resolution or with a particularly small primary beam stop.

In an advantageous further development of this method variant, an ion beam with circular cross-section and Gaussian distributed intensity is used in step b), the intensity maximum of which is on a symmetry axis of the beam-defining cross-sectional area of the pinhole of the single crystal aperture body. It is thereby prevented in a simple fashion that the (circular) round opening or the pinhole in the aperture body changes its shape due to post-processing. The ion beam that is irradiated along the symmetry axis has preferably a beam diameter (in accordance with FWHM, full width at half maximum) of at least half the desired diameter of the beam-defining cross-sectional area of the pinhole.

In one particularly preferred variant, the aperture is cleaned in an ultrasonic bath between step a) and step b), thereby reducing coarse soiling on the surface, which could not, or only with great difficulty, be removed by ion beam etching in step b). For this reason, ultrasonic bath cleaning also contributes to the reduction of parasitic scattering.

In an advantageous method variant, an opening facing away from the ion source, i.e. an inlet opening or the outlet opening of the X-ray aperture, is kept free. Material that has been removed can be discharged through the kept-free opening, which improves the effectiveness of the cleaning effect of ion beam etching.

In another preferred method variant, ions are exclusively directed onto the single crystal aperture body in step b). In particular, ions are not directed onto absorption structures, however, the overall ion beam or part thereof can radiate through the pinhole. This prevents soiling of the edge by foreign material (e.g. from the absorption structure).

In one advantageous method variant, the pinhole is introduced into the single crystal aperture body in step a) in such a fashion that the pinhole widens like a funnel starting from the edge in a second area towards an inlet opening of the X-ray aperture and that in step b) material is also removed from the surface of the aperture body in the second area by ion beam etching. A particularly large amount of single crystal material is then available for absorption in the area of the edge. Cleaning by ion beam etching also in the second area prevents an unnecessary increase in parasitic scattering due to roughness or defects on its side.

In another advantageous method variant, an ion beam is used in step b) which simultaneously irradiates several single crystal aperture bodies at the same time. Parallel processing reduces the time required for step b) for each aperture when large quantities are concerned, thereby reducing the production costs.

The present invention also concerns a method for post-processing an X-ray aperture, wherein the X-ray aperture comprises a aperture body that forms an edge for delimiting an X-ray beam, characterized in that material is removed from the surface of the aperture body at least in the area of the edge through ion beam etching. Ion beam etching reduces the defect density and the roughness in the area of the edge and also removes soiling (and a small amount of aperture material). This reduces parasitic scattering. The post-processing method is typically applied to single crystal aperture bodies. However, it can also be applied to polycrystalline aperture bodies in accordance with the invention. An X-ray aperture to be post-processed typically has only one aperture body, however, the invention may also be used for X-ray apertures comprising several aperture bodies.

In one advantageous variant of this method, the X-ray aperture has already been used in an X-ray analysis apparatus prior to material removal through ion beam etching. This yields initial improvement of the edge quality in terms of post-processing and also removes soiling accumulated during use of the X-ray aperture as well as generated defects.

In one preferred variant of the post-processing method, the aperture body is single crystal and has a through pinhole such that the edge on the single crystal aperture body is formed as a circumferential continuous edge that delimits the X-ray beam, starting from which edge the pinhole widens like a funnel in a first area towards an outlet opening, and material is also removed from the surface of the aperture body in the first area through ion beam etching, wherein the pinhole preferably has a round, in particular, circular cross-section at least in the area of the edge and of the first area. The edge quality of a single crystal aperture body can be improved to a particularly great extent through ion beam etching. The round pinhole geometry enables use of a round primary beam stop and improves the resolution compared with square beam cross-sections.

Further advantages of the invention can be extracted from the description and the drawing. The features mentioned above and below may be used in accordance with the invention either individually or collectively in arbitrary combination. The embodiments shown and described are not to be understood as exhaustive enumeration but have exemplary character for describing the invention.

The invention is illustrated in the drawing and is explained in more detail with reference to embodiments. In the drawing:

BRIEF DESCRIPTION OF THE DRAWING

FIG. 4b shows a schematic rear view of the X-ray aperture of FIG. 4a;

FIG. 7a shows a schematic cross-sectional view of an X-ray aperture with single crystal aperture body for the invention with an absorption structure on the front side which forms a holder that projects past the aperture body;

FIG. 7b shows a schematic rear view of the X-ray aperture of FIG. 7a;

FIG. 7c shows a schematic cross-sectional view of an X-ray aperture with single crystal aperture body for the invention, with an absorption structure on the rear side which forms a holder that projects past the aperture body;

FIG. 7d shows a schematic cross-sectional view of an X-ray aperture with single crystal aperture body for the invention, with a single crystal additional body and an absorption structure between the aperture body and the additional body, wherein the absorption structure forms a holder that projects past the aperture body;

FIG. 12a shows a schematic overview of a measurement system for determining the parasitic scattering of an X-ray aperture;

FIG. 12b shows a diagram that illustrates the parasitic scattering intensities of a polycrystalline X-ray aperture (▲), a single crystal X-ray aperture without ion etching (♦) and an inventive single crystal ion-etched X-ray aperture (x) with different overlaps of the X-ray beam with the X-ray aperture;

DESCRIPTION OF THE PREFERRED EMBODIMENT

Figure 1A:
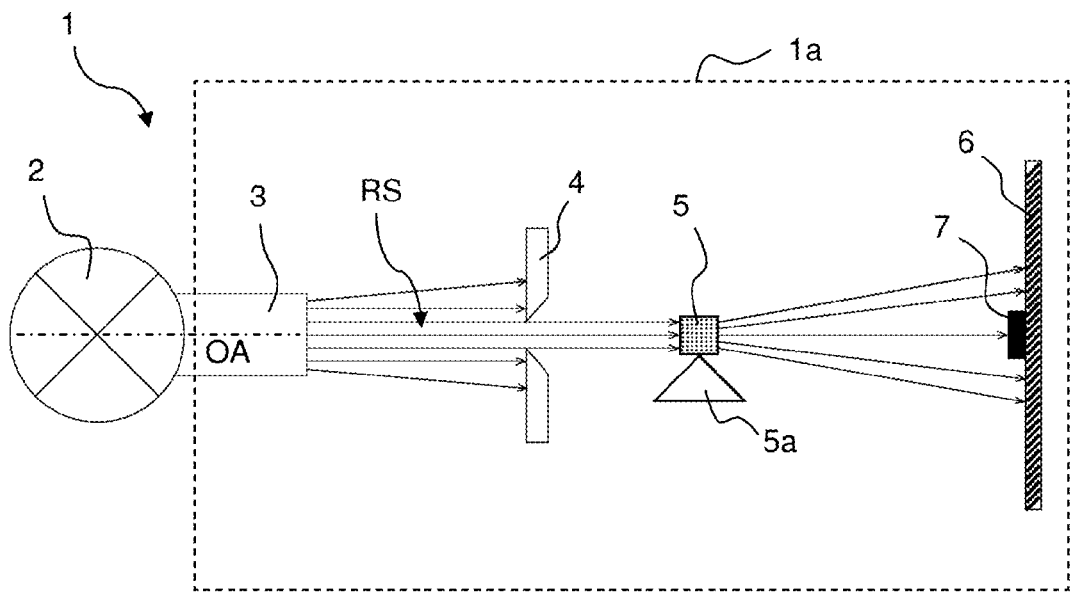
FIG. 1a shows a schematic overview of an inventive X-ray analysis apparatus comprising an X-ray aperture with single crystal aperture body.

The present invention presents a compact, scattering-free (or at least low-scattering) preferably round aperture for an X-ray analysis apparatus. The pinhole is also referred to as X-ray aperture. The aperture is advantageous in that it can be produced in an easy and reproducible fashion and can be integrated in and adjusted to existing and new X-ray analysis apparatus in an easy and inexpensive fashion, in particular, for SAXS, SCD and µ-XRD examinations.

Conventional production methods for X-ray apertures either cannot produce the required aperture design or introduce scattering centers into the aperture. For this reason, the invention also provides a production method for providing apertures for the invention.

In this connection, in particular, a special post-processing method (comprising surface treatment by ion beam etching) is used, which is followed by introducing an pinhole into a single crystal aperture body. The post-processing method can also be used to modify previously produced apertures (which have possibly already been used in an X-ray analysis apparatus) in such a fashion that they are free, or almost free, of scattering.

In accordance with the invention, a tunnel is introduced into a single crystal, which widens in the beam direction and advantageously has a round cross-sectional area, wherein the edge of the minimum and therefore beam-defining cross-sectional area of the tunnel forms an edge which is as sharp as possible.

The use of one single compact single crystal prevents parasitic scattering on grains, grain boundaries and on further defects. Moreover, parasitic scattering caused by total reflection is prevented or reduced in that the tunnel that widens in the beam direction has an opening angle which is larger than the total reflection angle and the edge at the border of the beam-defining cross-sectional area is as sharp as possible, ideally atomically sharp.

The outer dimensions of the single crystal may correspond to the commercially available, parasitically scattering polycrystalline apertures which are used in conventional X-ray analysis apparatus, for which reason the aperture can be exchanged quickly, easily and at little cost. An pinhole modification to an X-ray aperture which is arranged in an inventive X-ray analysis apparatus can also be realized quickly since, in contrast to conventional scattering apertures, the scattering-free (or at least low-scattering) apertures with single crystal aperture body can be aligned along the beam path more quickly, since the requirements for adjustment accuracy are less stringent. Slight misalignment does not or only minimally increase background radiation such that the signal-to-noise ratio is not substantially deteriorated.

The scattering-free (or at least low-scattering) apertures with single crystal aperture body can be produced in a few combinations of machining processes which are known per se. Mechanical reproducible and standardized introduction of a tunnel that widens in the beam direction can be easily realized with these combinations.

The inventive machining processes enable to also select a round cross-sectional area in addition to other shapes such that the resolution of SAXS analysis apparatus can be improved by more than 40% in comparison with scattering-free hybrid blade systems.

Within the scope of the invention, the pinhole is introduced by using only those machining processes which introduce defects substantially close to the surface of the single crystal, however, not or only to a limited extent at larger depths, in particular, electric discharge machining or cold laser ablation. Other methods such as e.g. drilling are not suited for this reason. The introduced defects as well as any soiling and large surface roughness cause relatively strong parasitic scattering. For this reason, in accordance with the invention, excessively accelerated ions are directed onto the single crystal surface in a post-processing step such that the ions remove the defective surface layers as well as absorbates and adsorbates and reduce the surface roughness. The associated reduction of the number of potential scattering centers also greatly improves the parasitic scattering behavior of the aperture, i.e. scattering is reduced.

Scattering-free (or at least low-scattering) pinholes based on a single crystal (i.e. based on a single crystal aperture body) enable reduction of the number of pinhole apertures in a SAXS structure to one or two, in consequence of which higher photon fluxes and smaller primary beam stops can be realized, which, in turn, increases the resolution and reduces the measuring times. The space requirements for a SAXS measuring instrument are also greatly reduced.

The inventive scattering-free apertures enable use of smaller primary beam stops in a SCD structure, which increases the resolution around the primary beam.

The scattering-free (or at least low-scattering) pinhole apertures that are based on a single crystal aperture body enable larger pinhole aperture diameters in a μ-XRD measuring arrangement, which results in higher photon fluxes and therefore shorter measuring times. The single crystal apertures moreover do not generate any Debye-Scherrer rings on the detector, which are superimposed on the measurement signal, but individual diffraction reflexes which can be unambiguously associated with the aperture material and therefore facilitate evaluation of the measured data.

Inventive X-Ray Analysis Apparatus

FIG. 1a shows a schematic view of a first embodiment of an inventive X-ray analysis apparatus 1. The X-ray analysis apparatus 1 can e.g. be used for a SAXS or SCD measurement.

The X-ray analysis apparatus 1 comprises an X-ray source 2, e.g. an X-ray tube, in the simplest case with a fixed anode. An X-ray beam RS emitted by the X-ray source 1 is reshaped by a beam-shaping element 3 (in the present case approximately parallelized by a Goebel or Montel mirror) and directed to an X-ray aperture 4. In the illustrated embodiment, the beam-shaping element 3 is directly mounted to the X-ray source 2 and the X-ray aperture 4 is disposed at a distance from the beam-shaping element 3.

The X-ray aperture 4 has a single crystal aperture body (in this connection see below, e.g. FIG. 2) and widens like a funnel in the propagation direction of the X-ray beam RS (in FIG. 1 from the left-hand side to the right-hand side, cf. optical axis OA). The X-ray aperture 4 blocks an outer part of the X-ray beam RS, wherein no or only very little parasitic scattering radiation is generated. For this reason, one X-ray aperture 4 is sufficient, at the same time keeping a low beam divergence. In case of an SCD measurement, the X-ray aperture 4 allows use of a very small primary beam stop (see below), thereby increasing the resolution.

The X-ray beam RS is then incident on a sample 5 which is held on a sample holder or goniometer 5a and is spaced apart from the X-ray aperture 4, typically at least by 1 cm in the beam propagation direction in SAXS and SCD measurements. The X-ray beam RS interacts with the sample 5 resulting in X-ray radiation emanating from the sample 5, which is registered by an X-ray detector 6. The X-ray detector 6 is designed as an area detector in the present case, which is, in turn, spaced apart from the sample 5 in the beam propagation direction, typically in a range of between 10 cm to 100 cm in SAXS measurements and typically at least 3 cm in SCD experiments. The detector 6 is thereby shadowed in a central area by a primary beam stop 7 such that transmitted undiffracted or unscattered X-ray radiation is not incident on the detector 6.

In the illustrated embodiment, the optical path of the X-ray radiation is substantially arranged in an evacuated housing 1a (wherein parts of the optical path may also be held under a protective gas atmosphere) in order to minimize air scattering.

Figure 1B:
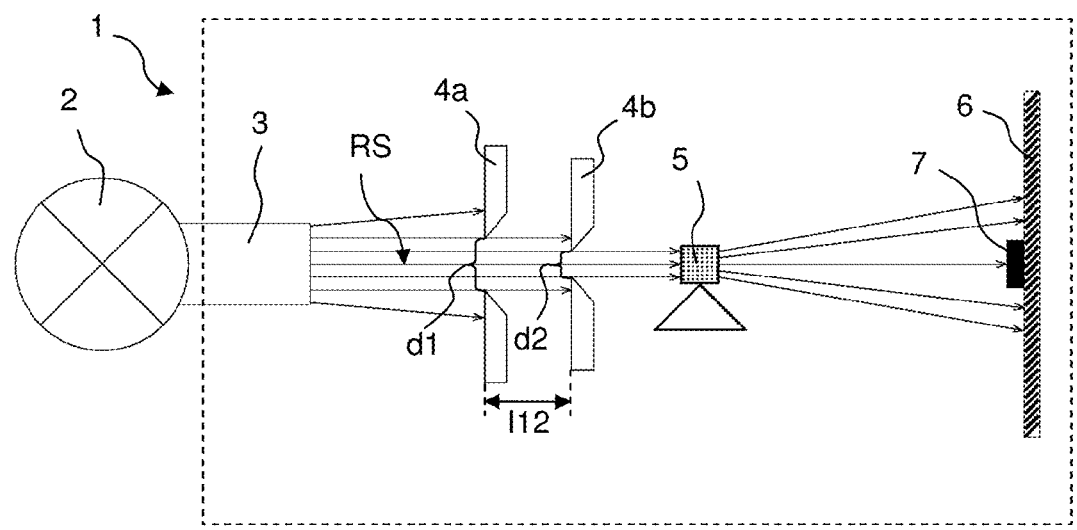
FIG. 1b shows a schematic overview of an inventive X-ray analysis apparatus comprising two X-ray apertures with single crystal aperture body.

FIG. 1b shows a second embodiment of an inventive X-ray analysis apparatus 1 which largely corresponds to the embodiment of FIG. 1a. For this reason, only the substantial differences are described below.

The X-ray analysis apparatus 1 has two X-ray apertures 4a, 4b with single crystal aperture body (see below), each of which widens like a funnel in the beam propagation direction. The X-ray apertures 4a, 4b each block an outer part of the X-ray beam RS, wherein no or only very little parasitic scattered radiation is generated.

The X-ray apertures 4a, 4b are arranged between the X-ray source 2 and the sample 5. Both X-ray apertures 4a, 4b are arranged at a separation from the sample 5. In SAXS measuring arrangements, the aperture diameters d1, d2 and the aperture separation l12 are selected in correspondence with the required divergence and the beam cross-section of the respective measuring arrangement (it should be noted that the aperture diameters d1, d2 of the X-ray apertures 4a, 4b can be selected to be equal or different, as in the illustrated case). The aperture diameters d1, d2 and the aperture separation l12 should be matched to the focus or the divergence of the X-ray source 2 in order to optimally utilize the power of the X-ray source 2. The separation between the X-ray aperture 4a and the sample 5 in the beam propagation direction is thereby typically at least 20 cm and the separation between the X-ray aperture 4b and the sample 5 in the beam propagation direction is typically at least 1 cm. In SCD experiments, the separation between the X-ray apertures 4a, 4b and the sample 5 in the beam propagation direction is typically is at least 8 cm (X-ray aperture 4a) and at least 1 cm (X-ray aperture 4b).

Figure 1C:
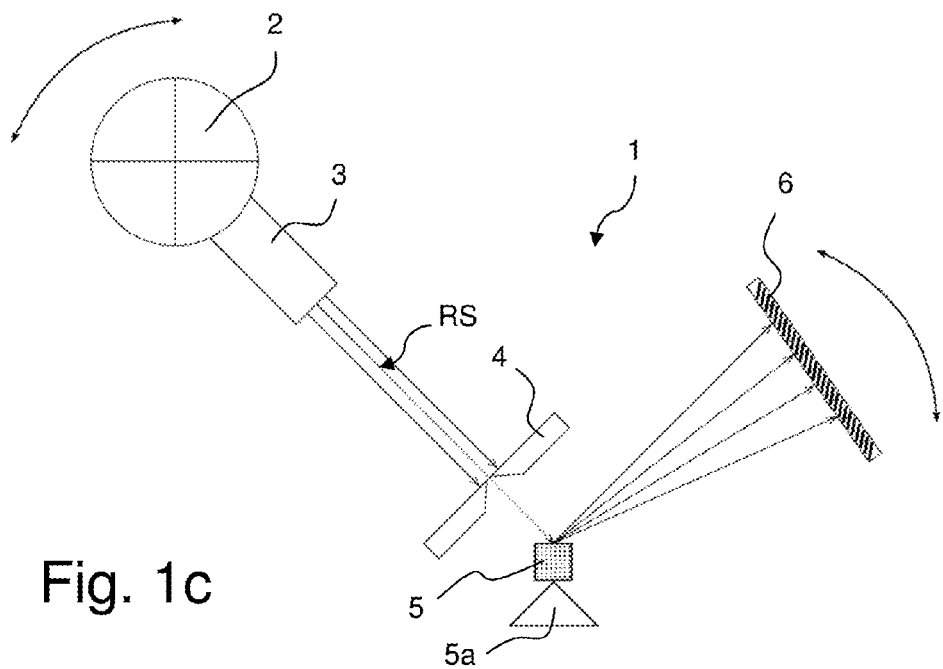
FIG. 1c shows a schematic overview of an inventive X-ray analysis apparatus comprising a aperture with single crystal aperture body, movable X-ray source and movable X-ray detector.

FIG. 1c schematically shows a top view of a third embodiment of an inventive X-ray analysis apparatus 1, which is particularly suited as a μ-XRD measuring arrangement. Also in this case, only the essential differences with respect to the embodiment of FIG. 1a are explained.

In this case, the X-ray source 2 can be rotated, together with the beam-shaping element 3 and the X-ray aperture 4 with single crystal aperture body, relative to the sample 5 on the sample holder 5a, wherein the associated axis of rotation extends perpendicularly to the plane of the drawing of FIG. 1c. The detector 6 can also be rotated about the same axis of rotation (goniometer structure). Since the X-ray aperture 4 with single crystal aperture body is used, it is possible to work with large aperture diameters or high photon fluxes, at the same time strictly delimiting the X-ray beam RS to the sample 5 or to a small area or a small volume of the sample 5.

Figure 2:
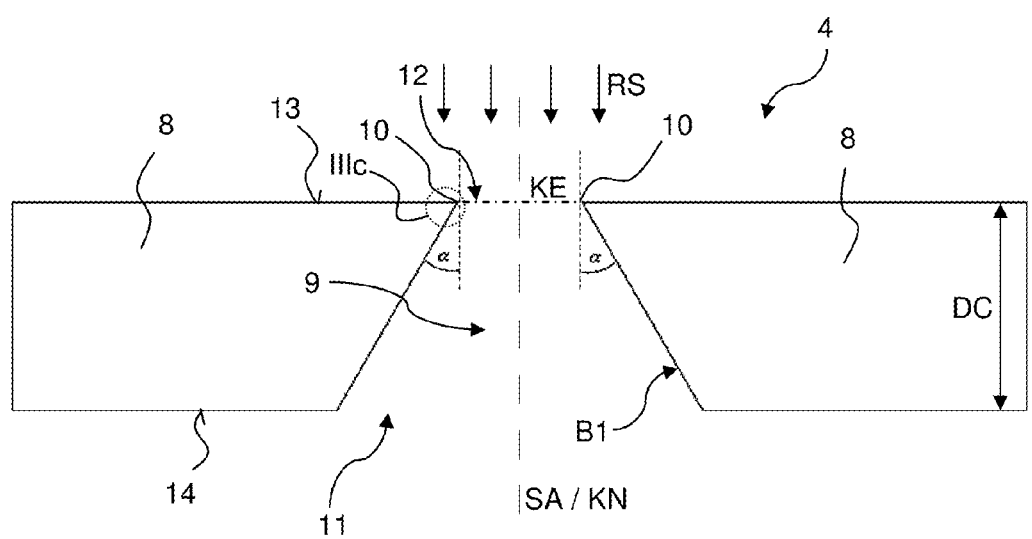
FIG. 2 shows a schematic cross-section of an X-ray aperture with single crystal aperture body for the invention, having a funnel-shaped first area.

FIG. 2 shows a cross-sectional view of an X-ray aperture 4 (which could be integrated in an X-ray analysis apparatus 1 of FIG. 1a or FIG. 1b) on the basis of a single crystal aperture body in accordance with the invention.

The X-ray aperture 4 comprises one single, single crystal (monocrystalline) aperture body 8 with a through pinhole 9. The pinhole 9 has a minimum diameter at a circumferential continuous edge 10. This edge 10 delimits an X-ray beam RS which is incident from above onto the X-ray aperture 4 in FIG. 2. The X-ray beam RS thereby propagates approximately parallel with respect to an axis of symmetry SA of the X-ray aperture 4. The circumferential edge 10 extends in this case in a plane (cf. edge plane KE, illustrated with dashed and dotted lines) perpendicular to the axis of symmetry SA (i.e. the edge plane surface normal KN extends parallel with respect to the axis of symmetry SA). The edge 10 determines the "beam-defining cross-sectional area" of the pinhole 9.

A first area B1 joins the edge 10 in the propagation direction of the X-ray beam RS, which area B1 widens like a funnel in the direction of an outlet opening 11 of the X-ray aperture 4. The first area B1 has a truncated shape in this case with an opening angle α of approximately 30° between the lateral area of the first area B1 and the axis of symmetry SA (FIG. 2 additionally shows auxiliary lines which are shifted in parallel with respect to the axis of symmetry SA in order to show the opening angle cc more clearly).

In the illustrated embodiment, the edge 10 defines at the same time an inlet opening 12 of the X-ray aperture 4. The front side (side of incidence) 13 of the aperture body 8 extends to the edge 10 perpendicularly to the axis of symmetry SA. In other words, the edge 10 is formed at the front side 13. The aperture thickness DC, i.e. the separation between the front side 13 and the rear side (outlet side) 14 of the X-ray aperture 4 or the aperture body 8 is typically in a range of between 0.1 mm to 3 mm, preferably 0.5 mm to 1.5 mm. The aperture body 8 is typically produced from Si or Ge (e.g. a single crystal wafer).

Figure 3A:
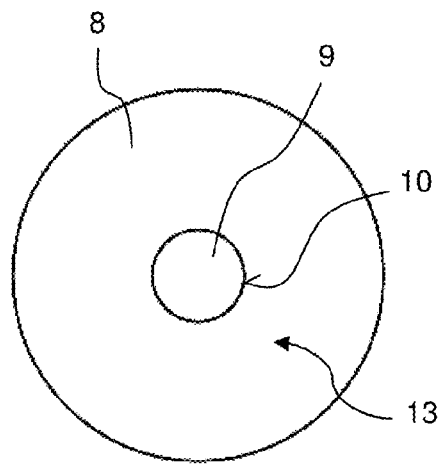
FIG. 3a shows a schematic front view of the X-ray aperture of FIG. 2 with round pinhole.
Figure 3B:
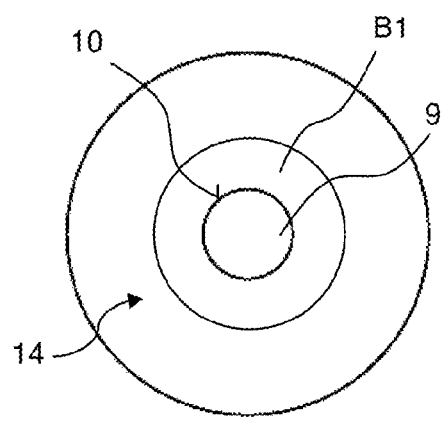
FIG. 3b shows a schematic rear view of the X-ray aperture of FIG. 2 with round pinhole.

The front side 13 and the rear side 14 of the aperture body 8 of the X-ray aperture of FIG. 2 are also shown in FIG. 3 (front view) and FIG. 3b (rear view), which each show the X-ray aperture 4 in a top view in a direction along the axis of symmetry SA (which extends perpendicularly to the image plane). The pinhole 9 has a circular cross-section both in the area of the edge 10 and in the first area B1, which enables use of a primary beam stop with minimum (circular) shadowing surface. The edge 10 is continuous over the entire periphery. The single crystal aperture body 8 is formed in one piece. The beam-defining cross-sectional area of the pinhole 9 is directly visible in each of FIGS. 3a and 3b.

Figure 3C:
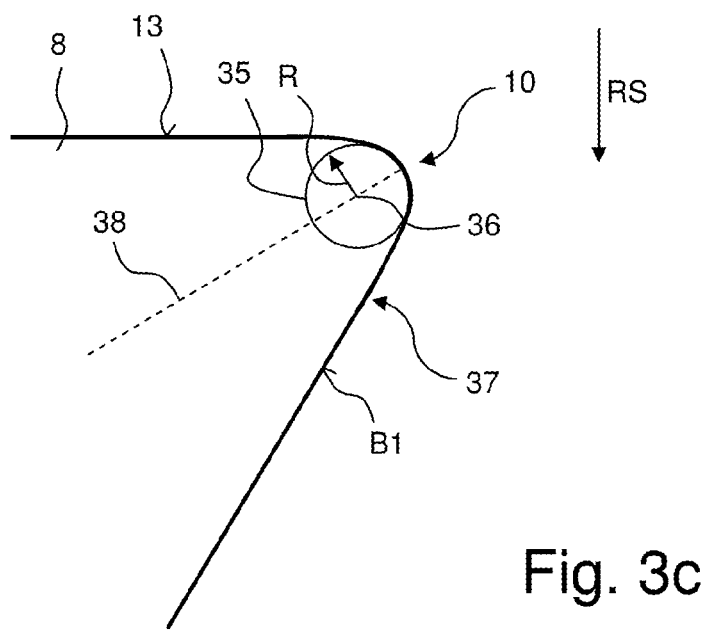
FIG. 3c shows a detailed section of FIG. 2 in the area of the edge.

FIG. 3c shows an enlarged section of the X-ray aperture illustrated in FIG. 2 (cf. dashed circular marking IIIc therein) in the area of the edge 10. In cross-section with the cross-sectional area parallel with respect to the direction of propagation of the X-ray beam RS or parallel to the axis of symmetry, one typically obtains a rounded profile 37 of the single crystal aperture body 8 in practice, wherein approximately straight profile sections (in the present case of the front side 13 and of the first funnel-shaped area B1) extend towards the edge 10 and are bent to merge into one another in the area of the edge 10.

The edge 10 is thereby advantageously formed to be as sharp as possible, preferably having an edge radius of less than 5 µm. The edge radius corresponds to the radius R of the greatest possible circle 35 which can be applied to the profile 37 from the inside (i.e. from the aperture body 8) without intersecting the profile 37. The center 36 of the circle 35 in the illustrated embodiment is on a bisector 38 between the straight profile sections of the front side 13 and the first area B1. The circle 35 abuts the profile 37 at least in the point of intersection between the bisector 38 and the profile 37. Due to the inventive post-processing method using ion etching, it is easily possible to form an edge 10 with an edge radius of less than 5 µm over the entire circumference of the pinhole.

Figure 4A:
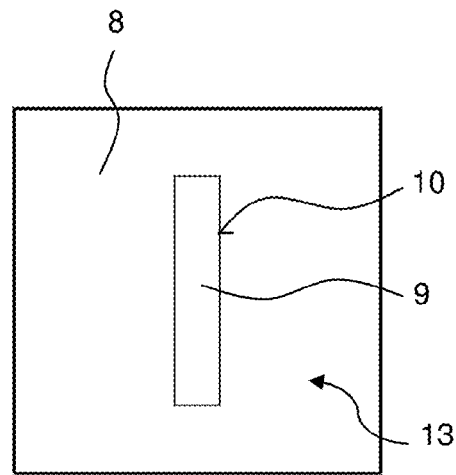
FIG. 4a shows a schematic front view of an X-ray aperture with single crystal aperture body with rectangular pinhole.
Figure 4B:
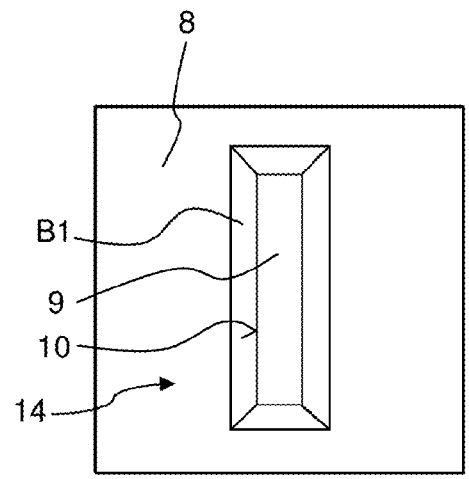

In one alternative embodiment of an X-ray aperture 4 with single crystal aperture body 8, the X-ray aperture 4 has a slotted pinhole 9 as illustrated in FIG. 4a in front view and in FIG. 4b in rear view. The first area B1 also extends in a funnel-shape in this case, however, with four flat perforated wall sections which are inclined with respect to the axis of symmetry (which extends perpendicularly with respect to the image planes). In this case, the circumferential edge 10 is also continuous and the single crystal aperture body 8 is in one piece. It should be noted that for producing the pinhole 9 having a rectangular cross-section, it is possible to use anisotropies in the material removal rate with respect to different directions of the crystal grid of the single crystal aperture body 8 in case of suitable orientation of the aperture body 8 and suitable aperture body material. FIGS. 4a and 4b again each directly show the beam-defining cross-sectional are of the pinhole 9.

Figure 5:
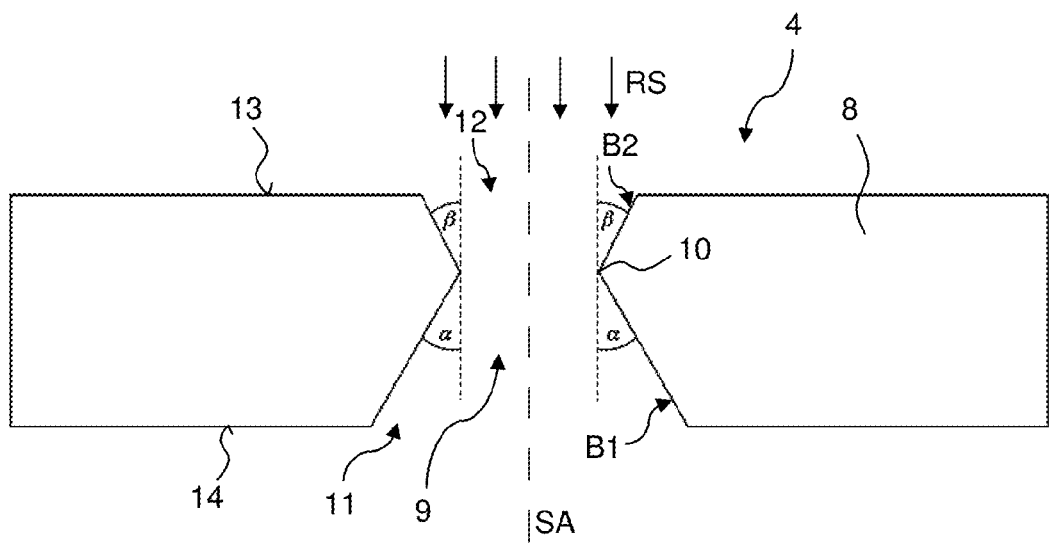
FIG. 5 shows a schematic cross-section of an X-ray aperture with single crystal aperture body for the invention with a funnel-shaped second area.

FIG. 5 shows a cross-sectional view of a further embodiment of an X-ray aperture 4 based on a single crystal aperture body 8, in which the pinhole 9 also widens like a funnel in said direction in a second area B2 which extends away from the edge 10 towards the inlet opening 12. In the second area B2, the pinhole 9 has a truncated shape (with circular cross-section which is not visible in FIG. 5) with an opening angle β of approximately 25°, measured between the lateral area in the second area B2 and the axis of symmetry SA of the X-ray aperture 4 (the angle β is illustrated in the figure by means of an auxiliary line that is shifted parallel to the axis of symmetry SA).

In the first area B1 the pinhole 9 extends as illustrated in FIG. 2.

Due to the two funnel-shaped areas B1 and B2 which join the edge 10, more absorbent material is arranged in the area of the edge 10 than in the embodiment of FIG. 2. This yields a more precise delimitation of the X-ray beam RS.

FIGS. 6a to 6d each show X-ray apertures 4 based on a single crystal aperture body 8 similar to FIG. 2, however, each having an absorption structure 15a-15d. The absorption structure 15a-15d is typically glued to the aperture body 8. The absorption structure 15a-15d is produced e.g. from polycrystalline lead.

Figure 6A:
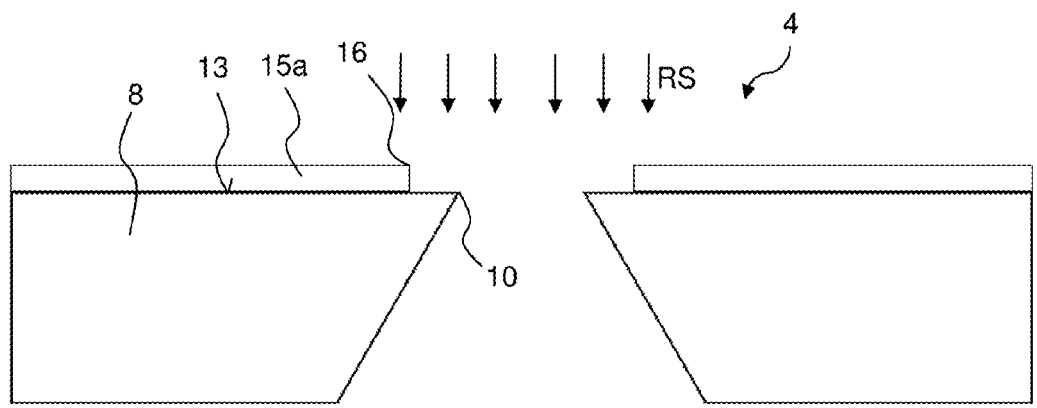
FIG. 6a shows a schematic cross-sectional view of an X-ray aperture with single crystal aperture body for the invention with an absorption structure on the front side.

The absorption structure 15a in FIG. 6a is arranged at the front side 13 of the X-ray aperture 4. It is recessed with respect to the edge 10 transversely to the beam propagation direction of the X-ray beam RS over the entire circumference, cf. the inner edge 16 of the absorption structure 15a. In the cross-sectional view of FIG. 6a, the inner edge 16 on the left-hand side of the X-ray aperture 4 is arranged further on the left than the inner edge 10. This equally applies to the right-hand side of the X-ray aperture 4. This ensures that X-ray radiation scattered on the absorption structure 15a, in particular, on the inner edge 16, can be blocked by the aperture body 8.

Figure 6B:
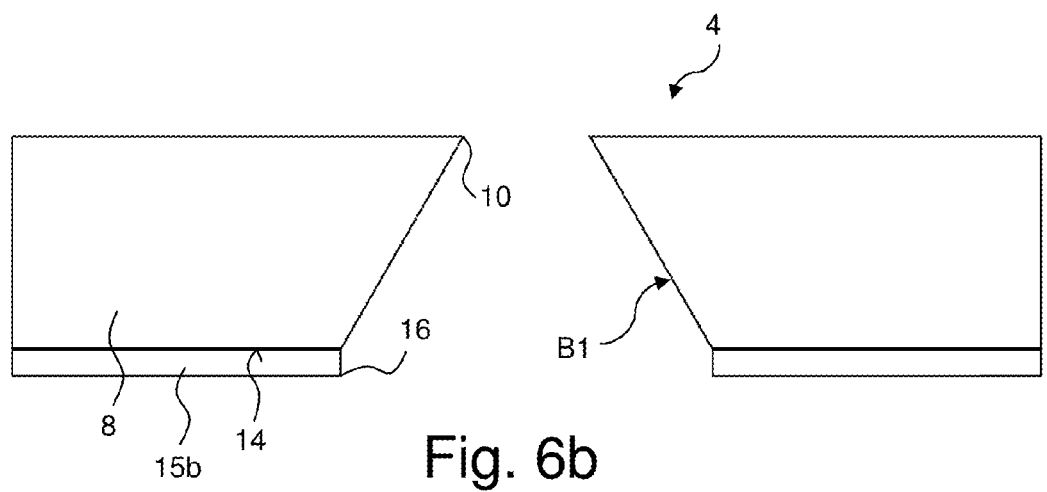
FIG. 6b shows a schematic cross-sectional view of an X-ray aperture with single crystal aperture body for the invention with an absorption structure on the rear side.

The absorption structure 15b in FIG. 6b is arranged at the rear side 14 of the X-ray aperture 4. Although the absorption structure 15b covers the overall rear side 14, it is also ensured in this case that the inner edge 16 is recessed with respect to the edge 10 of the aperture body 8 due to the widening first area B1.

Figure 6C:
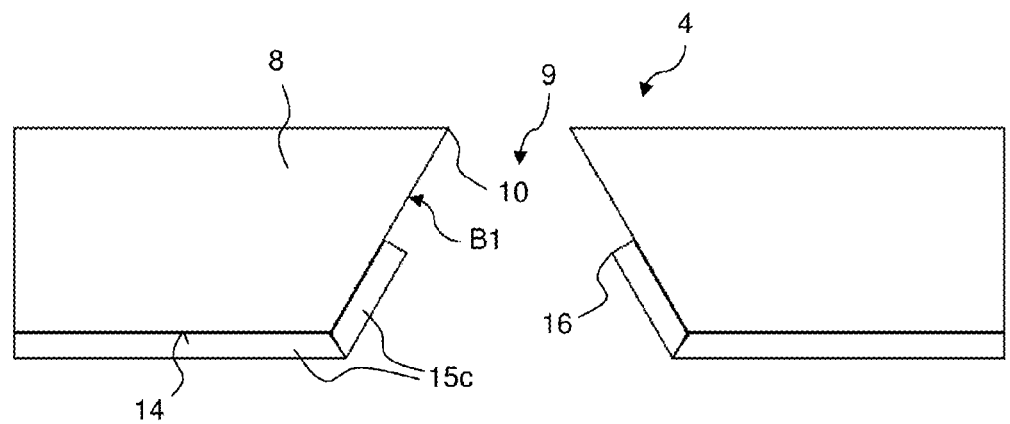
FIG. 6c shows a schematic cross-sectional view of an X-ray aperture with single crystal aperture body for the invention with an absorption structure on the rear side and a rear part of the funnel-shaped first area.

In the absorption structure 15c of FIG. 6c, part of the funnel-shaped first area B1 of the pinhole 9 is also lined in addition to the rear side 14. For this reason, the inner edge 16 moves radially slightly closer to the edge 10 of the aperture body 8. However, the inner edge 16 is also recessed with respect to the edge 10 in this case.

Figure 6D:
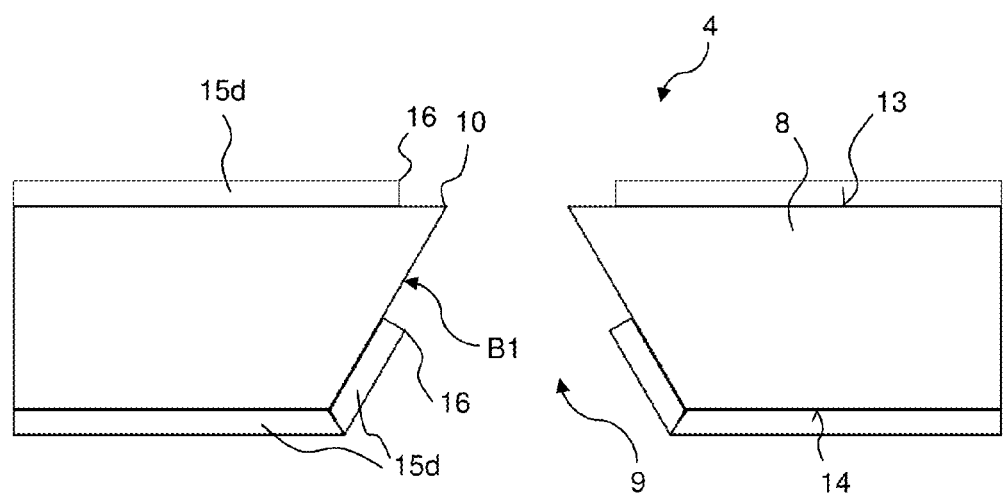
FIG. 6d shows a schematic cross-sectional view of an X-ray aperture with a single crystal aperture body for the invention, with an absorption structure on the front side, on the rear side and on a rear part of the funnel-shaped first area.

The absorption structure 15d of FIG. 6d finally covers the major part of the front side 13, a rear part of the first area B1 and the rear side 14 of the aperture body 8. This ensures maximum absorption of X-ray radiation that does not pass the pinhole 9. Both inner edges 16 of the absorption structure 15d are recessed with respect to the edge 10.

FIG. 7a illustrates a further embodiment of an X-ray aperture 4 on the basis of a single crystal aperture body 8, which comprises an absorption structure 15e at the front side 13, which is similar to that illustrated in FIG. 6a, wherein, however, the absorption structure 15e projects outwardly in a direction transverse to the direction of propagation of the X-ray beam RS past the aperture body 8, thereby forming a holder 17. The holder 17 can e.g. be engaged by clamps (not shown) in order to hold the X-ray aperture 4, thereby preventing mechanical load on the single crystal of the aperture body 8 (which is e.g. produced from silicon or germanium) and which is usually fragile. It should be noted that another circular pinhole 9a is formed in the absorption structure 15e in the area of the circular pinhole 9 of the aperture body 8, which defines the inner edge 16 of the absorption structure 15e. FIG. 7b shows the X-ray aperture 4 of FIG. 7a in a rear view (perpendicular to the beam propagation direction).

FIG. 7c shows an X-ray aperture 4 similar to FIG. 6b with an absorption structure 15f on the rear side, wherein the absorption structure 15f projects again past the aperture body 8 to form a holder 17.

FIG. 7d shows an X-ray aperture 4 with single crystal aperture body 8 for the invention, in which a single crystal additional body 18 is used. The additional body 18 and the aperture body 8 are mounted, typically glued, to opposite sides of the absorption structure 15g. The edge 10, which delimits the X-ray beam RS, is formed on the aperture body 8. The inner edge 16 of the absorption structure 15g is recessed with respect to the edge 10. The absorption structure 15g again forms holders 17 which laterally project past the aperture body 8. The material of the additional body 18 is usually selected to be different from the material of the aperture body 8 in order to be able to compensate for weaknesses of the aperture body material, e.g. for different applications using X-ray radiation of different wavelengths.

In all embodiments, the holders 17 can form grooves, projections, depressions, threads or the like in order to facilitate mounting of the X-ray aperture 4.

Figure 8A:
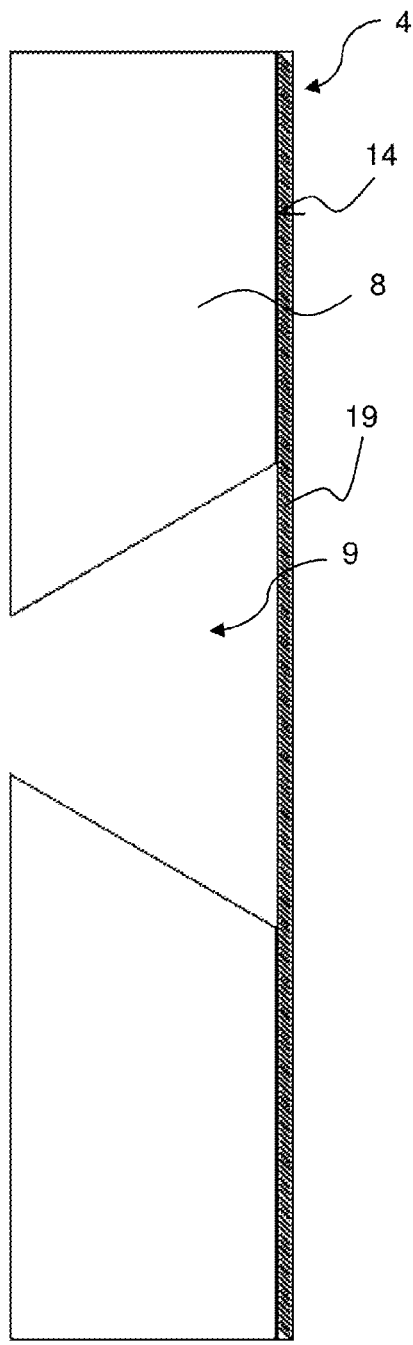
FIG. 8a shows a schematic cross-sectional view of an X-ray aperture with single crystal aperture body for the invention, with a cover structure on the rear side.

FIG. 8a shows an X-ray aperture 4 with a single crystal aperture body 8 for the invention, which comprises a cover structure 19. In the illustrated embodiment, it is arranged on the rear side 14 of the aperture body 8 and completely covers the pinhole 9 such that it is sealed in a gas-tight and vacuum-tight fashion. The cover structure 19 typically consists of beryllium or kapton. The X-ray aperture 4 can be used as X-ray window due to the cover structure 19 and can separate parts of the optical path of different gas pressure levels. The cover structure 19 is typically glued onto the aperture body 8.

Figure 8B:
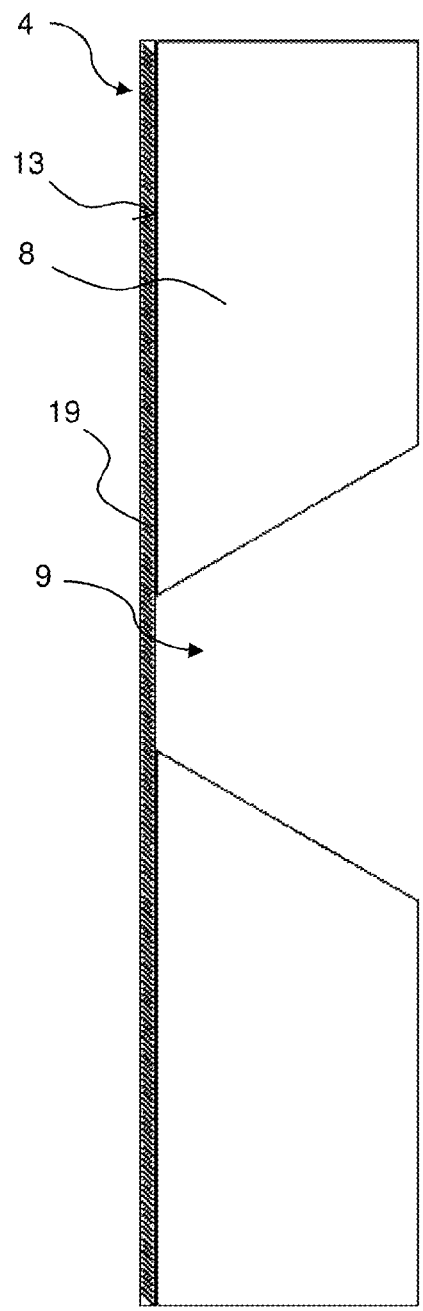
FIG. 8b shows a schematic cross-sectional view of an X-ray aperture having a single crystal aperture body for the invention, with a cover structure on the front side.

As can be gathered from FIG. 8b, the cover structure 19 may alternatively also be arranged at the front side 13 of the aperture body 8 in order to seal the pinhole 9.

Figure 9:
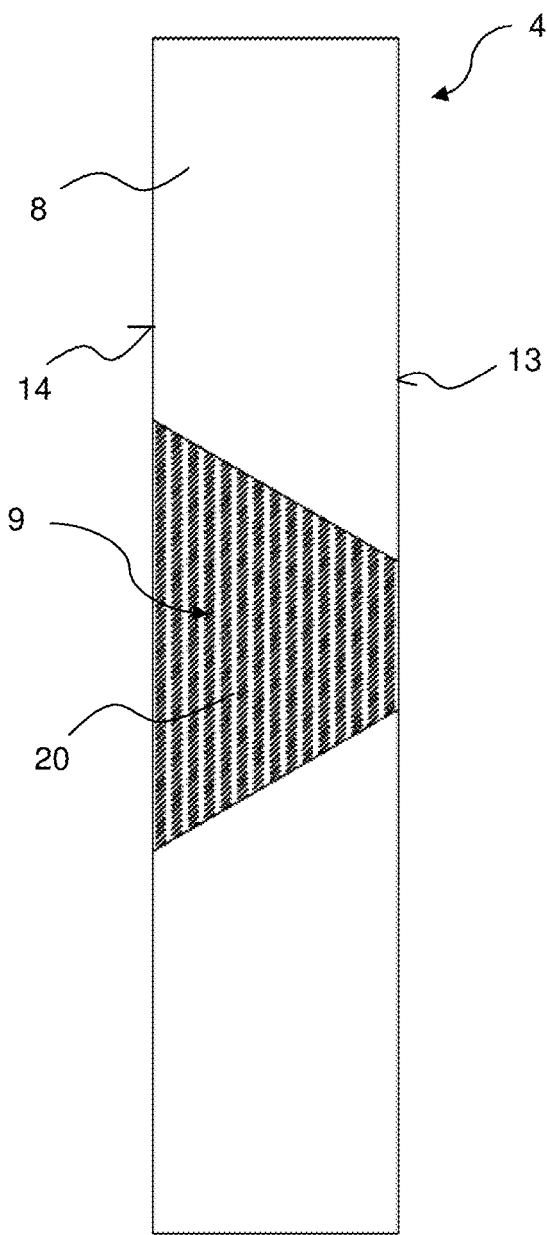
FIG. 9 shows a schematic cross-sectional view of an X-ray aperture with single crystal aperture body for the invention, with a fill structure in the pinhole of the aperture body.

FIG. 9 further shows an X-ray aperture 4 with single crystal aperture body 8 for the invention, in which a fill structure 20 fills the through pinhole 9. The fill structure 20 consists of a material which has poor X-ray absorption properties (in comparison with the material of the aperture body 8), e.g. beryllium or kapton. In the illustrated embodiment, the fill structure 20 is flush with the front side 13 and also with the rear side 14 of the aperture body 8.

Figure 10A:
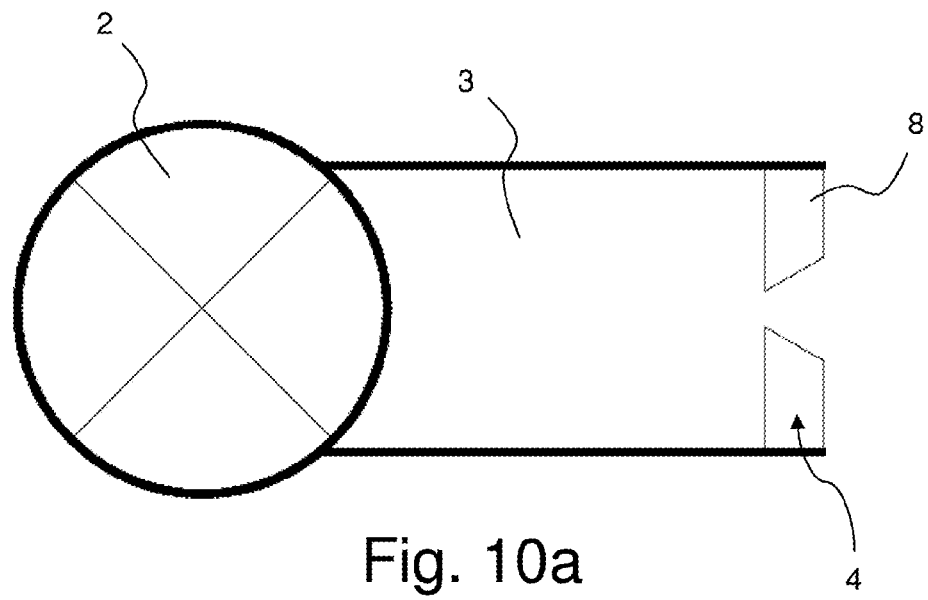
FIG. 10a shows a schematic view of an X-ray tube with beam-shaping optics and an X-ray aperture, mounted thereto and comprising a single crystal aperture body for an inventive X-ray analysis device.

FIG. 10a schematically shows part of an inventive X-ray analysis apparatus in the area of the X-ray source 2. The X-ray source 2 is directly connected to a beam-forming component 3, at the outlet opening of which facing away from the source, an X-ray aperture 4 with single crystal aperture body 8 is arranged. An X-ray beam defined by the X-ray aperture 4 can be directed directly onto a sample, which provides a particularly compact construction.

Figure 10B:
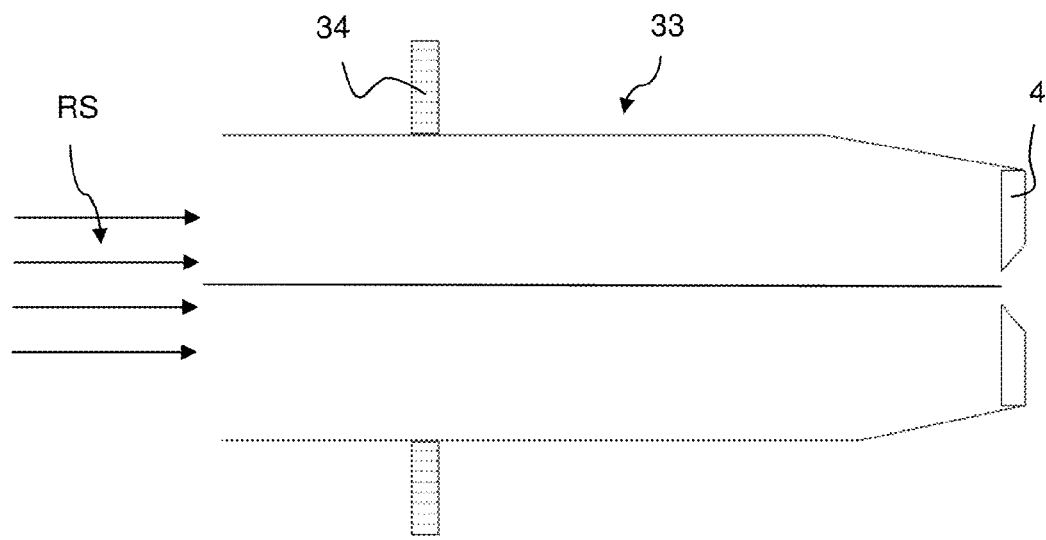
FIG. 10b shows a schematic view of a aperture with an X-ray aperture with single crystal aperture body for the invention.

FIG. 10b shows a aperture 33 as it can be used in SCD and μ-XRD measuring arrangements or in a corresponding inventive X-ray analysis apparatus, e.g. between the X-ray source and the sample. The aperture 33 is mainly used as a holder for an X-ray aperture 4 on the outlet side with a single crystal aperture body (as illustrated e.g. in FIG. 2) and is itself mounted to a holder 34. The aperture 33 or the X-ray aperture 4 contained therein are used to delimit the X-ray beam RS.

Figure 10C:
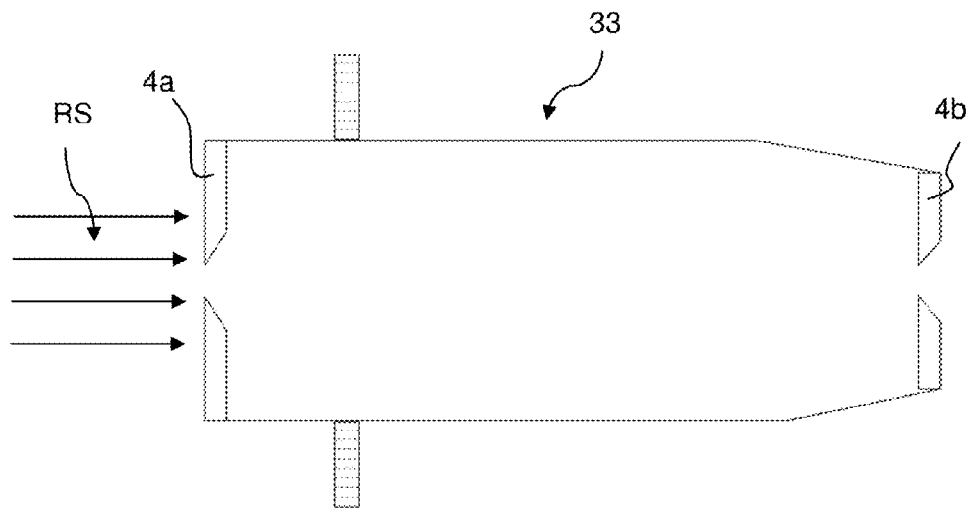
FIG. 10c shows a schematic view of a aperture, with two X-ray apertures with single crystal aperture body for the invention.

FIG. 10c shows an embodiment of a aperture 33 similar to FIG. 10b, however, comprising two X-ray apertures 4a, 4b, with single crystal aperture body. The divergence of the X-ray beam RS can be adjusted by means of the separation between the two X-ray apertures 4a, 4b and by means of their pinhole diameters.

Inventive Production Method or Post-Processing Method for an X-Ray Aperture

In accordance with the invention, scattering-free (or at least low-scattering) X-ray apertures can be produced which are based on a single crystal aperture body. The low parasitic scattering does not only result from the use of a single crystal aperture body but also from the performance of the production method. The inventors have found out that certain method steps are of decisive importance for low parasitic scattering, in particular, a post-processing step after introduction of the through pinhole into the aperture body. FIGS. 11a to 11d illustrate the inventive post-processing method.

Ion beam etching (herein also briefly referred to as ion etching), which is presented below, can be used within the scope of the inventive production of an X-ray aperture with single crystal aperture body or can also be used for the inventive post-processing of an existing X-ray aperture which e.g. has already been used in an X-ray apparatus and the edge quality of which is deteriorated due to constant X-ray radiation bombardment and dirt deposits.

Figure 11A:
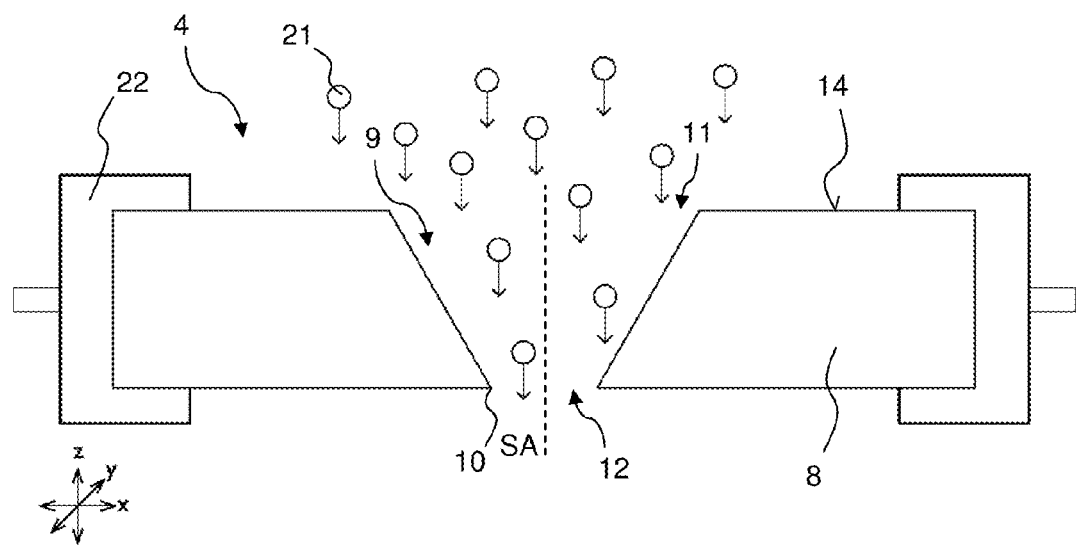
FIG. 11a shows a schematic cross-sectional view of a single crystal aperture body which is held in clamp-like lateral guidances during inventive post-processing using ion etching from the rear side.

In accordance with the invention, for post-processing a aperture body 8, which already has a through pinhole 9, ions 21, preferably $Ar^+$ ions or other inert gas ions are fired with high kinetic energy, typically using an acceleration voltage in a range of between 0.1 kV and 20 kV, onto the aperture body 8, cf. FIG. 11a ("ion etching").

Towards this end, an ion source (not shown) typically emits an ion beam whose cross-sectional area is larger than the cross-sectional area of the opening of the aperture body 8 facing the ion source (in the present case the outlet opening 11) in order to ensure complete processing of the aperture body surface of the pinhole 9 facing the opening up to the edge 10. The ion beam usually has a rotationally symmetrical Gaussian distributed intensity profile. The cross-sectional area of the ion beam results from the drop to half the maximum intensity. If the ion beam has a smaller cross-sectional area than the opening of the X-ray aperture 4 facing the ion source, the ion beam can also be moved relative to the X-ray aperture 4 (in FIG. 11a in x and y direction "parallel" to the X-ray aperture 4) in order to ensure complete processing. The ion beam cross-section can be adjusted by changing the separation between the ion source and the aperture body 8, i.e. by a relative motion in z direction.

The ion beam is preferably aligned parallel to the axis of symmetry SA of the X-ray aperture or perpendicular to the side facing the ion source (in the present case the rear side 14) of the aperture body 8 in order to ensure uniform removal of material. (If the shape of the pinhole needs to be corrected after introducing the pinhole 9, it is also possible to pivot the ion source such that the ion beam is tilted in a suitable fashion with respect to the axis of symmetry SA). In order not to change the shape of the inlet opening 12 or of the pinhole 9, in case of a Gaussian distributed ion beam intensity, the intensity maximum is preferably on the axis of symmetry SA and the ion beam cross-section has also preferably the same shape as the opening cross-section in the single crystal aperture body 8. For post-processing of circular opening cross-sections in the single crystal aperture body 8, the ion beam cross-section should therefore also preferably be selected to be circular. If desired, the shape can also be corrected through an offset of the intensity maximum (in the xy plane) with respect to the axis of symmetry SA.

In FIG. 11a, the aperture body 8 is laterally held by clamps 22 on which the ion beam is not incident. The opening facing away from the ion source (in the present case the inlet opening 12) is not covered such that removed material can easily escape through the opening. The opening preferably faces in a downward direction such that gravity promotes falling down of the removed material. If a cover structure is desired (cf. FIGS. 8a, 8b) it is disposed only after termination of ion etching. Absorption structures, in particular, with holder, can be mounted selectively prior to or (preferably) after ion etching.

Figure 11B:
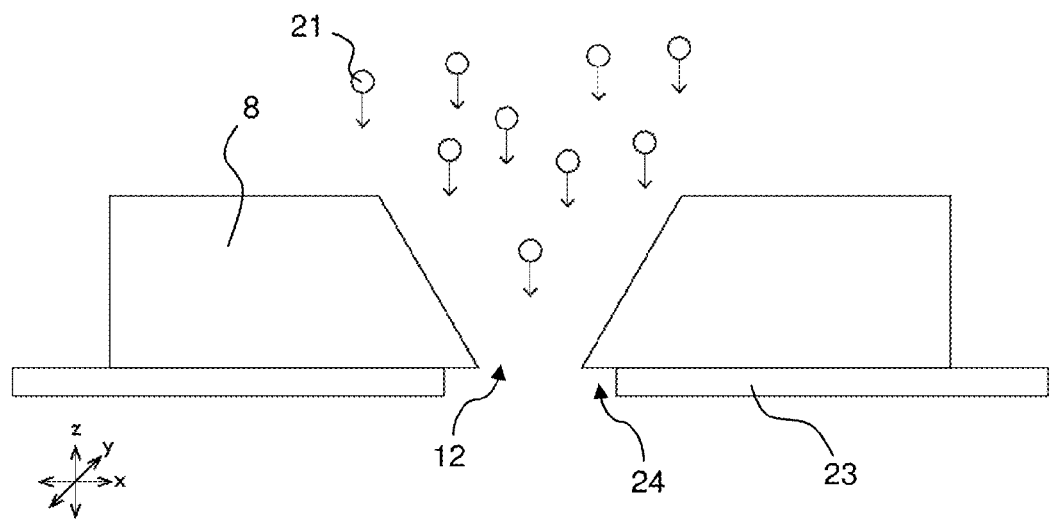
FIG. 11b shows a schematic cross-sectional view of a single crystal aperture body that is supported on a perforated support plate during inventive post-processing using ion etching from the rear side.

It is also possible to support the aperture body 8 on a support plate (substrate holder) 23 during ion etching, cf. FIG. 11b. The support plate 23 has an pinhole 24 in order not to cover the opening facing away from the ion source (in the present case the inlet opening 12).

Figure 11C:
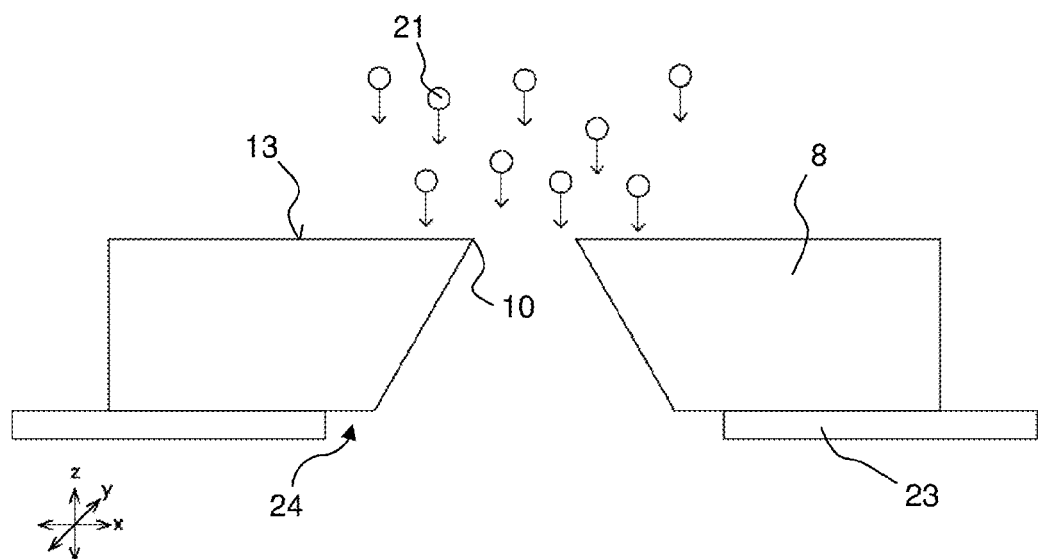
FIG. 11c shows a schematic cross-sectional view of a single crystal aperture body that is supported on a perforated support plate during inventive post-processing using ion etching from the front side.

After processing from the rear side 14, as illustrated e.g. in FIG. 11b, processing from the front side 13 may follow, as illustrated in FIG. 11c (or vice versa). In this fashion, removal of soiling and near-surface defects from the edge 10 and its direct vicinity is further facilitated. The aperture body 8 can be disposed onto a support plate 23 with sufficiently large pinhole 24 also for this purpose.

Figure 11D:
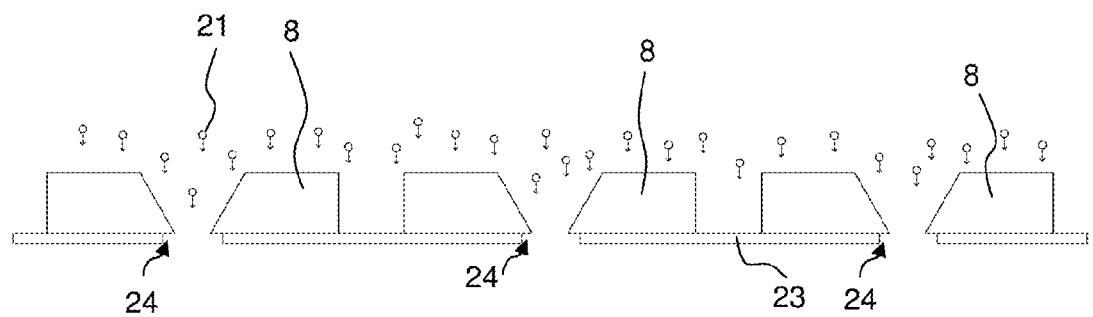
FIG. 11d shows a schematic cross-sectional view of several single crystal aperture bodies that are supported on a common multiply perforated support plate during simultaneous inventive post-processing using ion etching from the rear side.

For producing large quantities of X-ray apertures, it is also possible to process several aperture bodies 8 at the same time with a correspondingly large ion beam, as illustrated in FIG. 11d. Towards this end, the aperture bodies 8 can be arranged on a common support plate 23 with several pinholes 24.

Figure 11E:
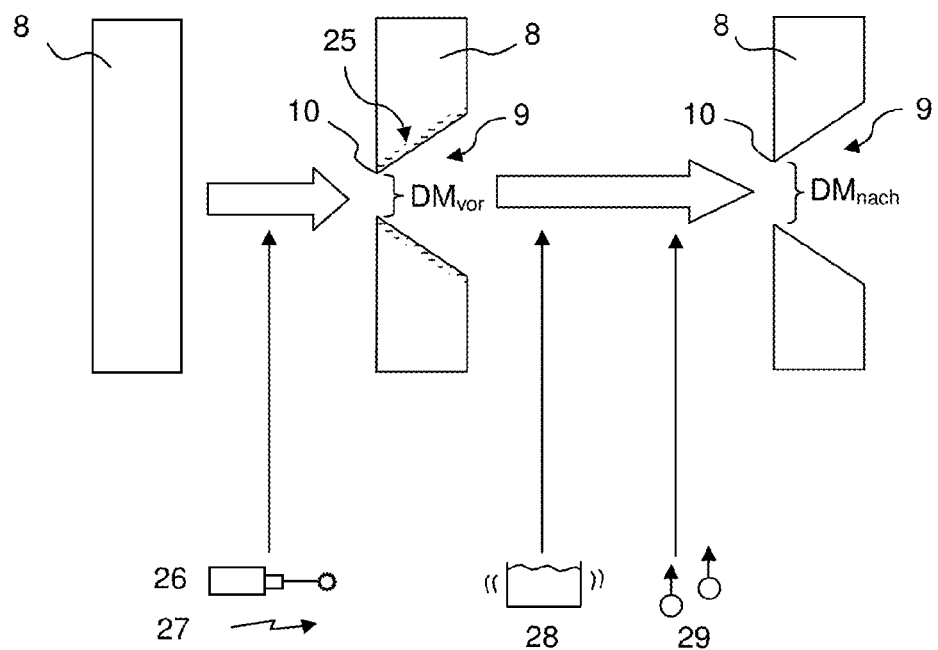
FIG. 11e shows a schematic overview of the inventive production process of an X-ray aperture with single crystal aperture body.

FIG. 11e gives an overview of the overall process of an inventive production method for X-ray apertures with a single crystal aperture body 8.

At first, a single-piece single crystal aperture body 8 is provided, e.g. by cutting a corresponding piece out of a wafer.

Then, a continuous pinhole 9 is introduced into the aperture body 8 using a suitable method, in particular, cold laser ablation 26 and/or electric discharge machining 27. This is accompanied by generation of defects in a near-surface material layer 25 in the single crystal aperture body 8 (however, not in deeper layers, e.g. deeper than 20 to 40 μm). Further results are a certain amount of surface soiling and increased roughness.

For this reason, the aperture body 8 is subsequently cleaned in an ultrasonic bath 28 and the defective near-surface material layer 25 in the area of the pinhole 9 is finally removed by ion etching 29 and the roughness is reduced, in particular, in a wavelength range of 0.1 nm to 10 μm. The latter measure increases the beam-defining cross-sectional area which is defined by the edge 10. The smallest pinhole diameter increases from $DM_{vor}$ to $DM_{vor}$ by typically approximately 20-200 μm, usually by 100 μm.

The aperture body 8 or its edge 10 can then be used to delimit an X-ray beam with, at best, very low parasitic X-ray radiation.

Experimental Proof of the Inventive Effect

Experimental data concerning the parasitic scattering behavior of different X-ray apertures is presented below, including an X-ray aperture based on a single crystal aperture body, which has been post-processed in accordance with the invention.

In order to determine the parasitic scattering behavior of different X-ray apertures, a measuring arrangement is used, as illustrated in FIG. 12a. The aperture 30 to be investigated is successively moved into an X-ray beam RS which is approximately parallel (divergence=0.7 mrad, beam cross-section—full width at half maximum=0.25 mm) with Gaussian intensity distribution with a step size of 10 μm. The parasitic scattering signal (cf. the parasitic scattered radiation 32) of the edge 10 can thereby be measured with a scattering angle of more than 1 mrad at the detector 6 around the primary beam stop 7.

In order to determine the portion of light that passes through the aperture 30 in relation to the overall intensity of the X-ray beam ($Int_{pass}/Int_{total}$), a piece of glass-like carbon 31 is used as reference material. This is a material that is well known in science, is stable and has reproducible scattering properties. When the overall intensity of the X-ray radiation (the aperture 30 is thereby completely removed from the optical path) is incident on the glass-like carbon 31, the latter generates a characteristic scattering intensity $Int_{total}$. It is used as a reference value for determining unknown photon fluxes.

In order to determine the X-ray radiation intensity that passes through the aperture 30, the glass-like carbon 31 is positioned in the optical path after each movement of the aperture 30 and measurement of the parasitic scattering intensity 32 of the edge 10. Thereupon, the glass-like carbon 31 generates a scattering intensity $Int_{pass}$ from which $Int_{pass}/Int_{total}$ can be calculated. The ratio $Int_{pass}/Int_{total}$ thereby corresponds directly to the portion of the X-ray radiation that passes through the aperture 30 in relation to the overall irradiated X-ray radiation intensity (with the aperture 30 being completely removed from the optical path). In contrast thereto, air scattering and dark current of the detector 6 are subtracted from the parasitic scattering intensity 32 generated by the edge 10 and detected by the detector 6. This parasitic scattering intensity is subsequently normalized to an overall intensity that is typical for the measuring system so that measurements of different apertures 30 can be compared.

FIG. 12b shows the normalized parasitic scattering intensity (linearly plotted towards the top in arbitrary units, bE) for different portions $Int_{pass}/Int_{total}$ of the X-ray radiation that has passed through the aperture 30 (linearly plotted towards the right, between 0 and 1) for different apertures:

a commercially available polycrystalline X-ray aperture of platinum/iridium; circular pinhole cross-section with a diameter of 750 μm; α=45°, β=90°; (symbol ]);

an X-ray aperture with single crystal aperture body of germanium, produced through cold laser ablation without post-treatment by ion etching; circular pinhole cross-section with a diameter of 450 μm; α=15°; β=90°; (symbol ♦);

an X-ray aperture with single crystal aperture body of germanium, produced through cold laser ablation with post-treatment by ion etching; circular pinhole cross-section with a diameter of 550 μm; α=15°; β=90°; (symbol X).

A total of two measuring cycles were performed for each aperture at different edge positions, which are respectively shown in FIG. 12b.

At the start of the respective measuring cycles, no X-ray radiation passes through the opening ($Int_{pass}/Int_{total}$=0) which gradually changes in the further course ($Int_{pass}/Int_{total}$>0). With each step, the amount of X-ray photons that are incident on the beam-shaping edge increases, which X-ray photons are parasitically scattered thereon to a greater or lesser degree in dependence on the aperture. With $Int_{pass}/Int_{total}$=0.5, the maximum number of photons is incident on the edge and generates the greatest scattering signal. The scattering behavior of the different apertures can be compared very well here. The parasitic scattering is reduced in accordance with the Gaussian distributed radiation intensity in the further course.

As can be gathered from FIG. 12b with $Int_{pass}/Int_{total}$=0.5, the parasitic scattering can already be reduced from approximately 150-200 bE to approximately 100 bE, i.e. by half, using a single crystal X-ray aperture without ion etching compared to a conventional polycrystalline aperture. When the single crystal X-ray aperture is additionally subjected to post-treatment by ion etching, the parasitic scattering decreases to such a large extent that the measurement inaccuracy is obtained. For $Int_{pass}/Int_{total}=0.5$, the experiment determined 4 bE, i.e. one fiftieth of the value of the polycrystalline aperture. This suggests that the Q value is high and the aperture produced in accordance with the invention is free of scattering (or almost free of parasitic scattering).

Figure 12C:
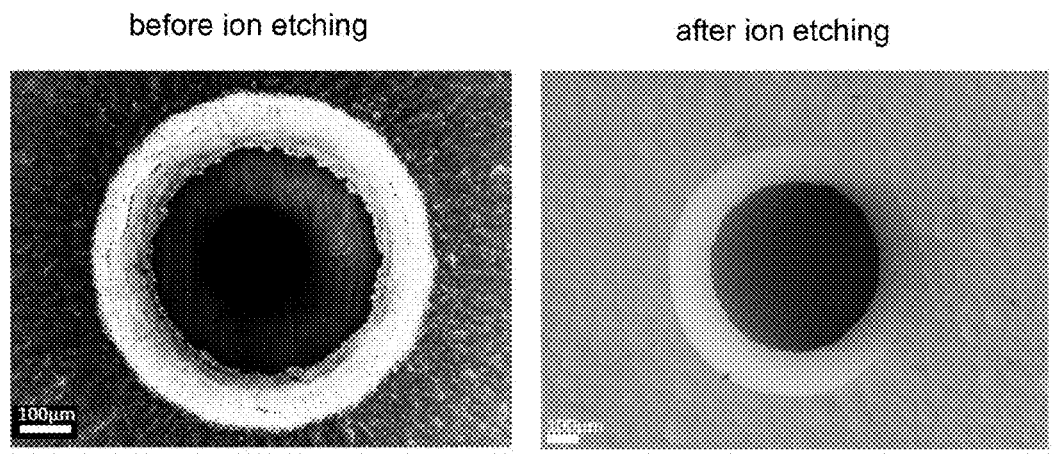
FIG. 12c shows REM images of the rear side of a single crystal X-ray aperture for the invention prior to ion etching (left-hand side) and after ion etching (right-hand side)
Figure 12D:
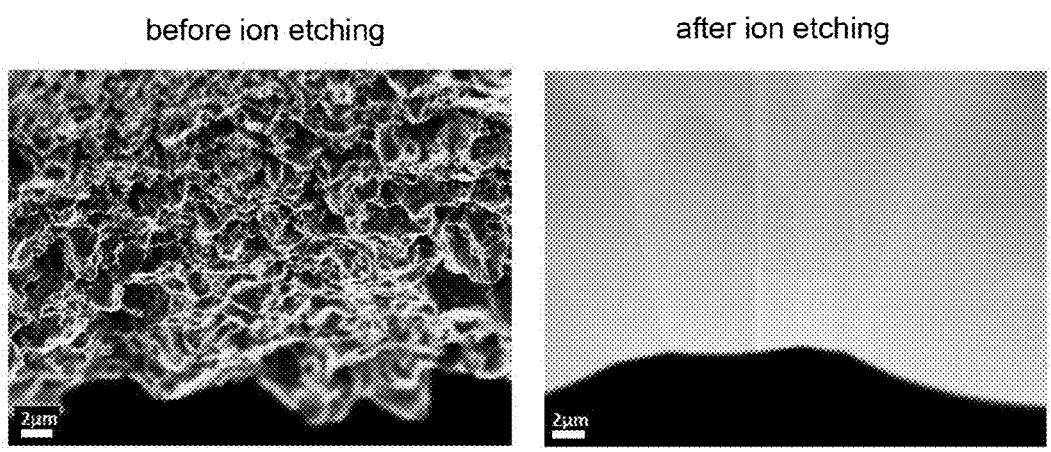
FIG. 12d shows REM images of the edge of a single crystal X-ray aperture for the invention prior to ion etching (left-hand side) and after ion etching (right-hand side).

Scanning electron microscopic images have shown that the surface roughness of X-ray apertures with single crystal aperture bodies is considerably reduced and the edge sharpness can be increased by ion etching. Towards this end, FIG. 12c shows a rear side of a single crystal aperture body in the area of the pinhole prior to ion etching (left-hand side) and after ion etching (right-hand side). FIG. 12d shows an enlarged section of the respective edge of the pinhole, again prior to ion etching (left-hand side) and after ion etching (right-hand side).

We claim:

1. An X-ray analysis apparatus comprising:
    an X-ray source from which an X-ray beam is emitted;
    at least one X-ray aperture which delimits said X-ray beam emitted by said X-ray source, said at least one X-ray aperture having a single crystal aperture body with a through pinhole, wherein said single crystal aperture body consists of one single piece of monocrystalline material, said single crystal aperture body forming a continuous circumferential edge which delimits said X-ray beam and starting from which said pinhole widens like a funnel in a direction of an outlet opening of said X-ray aperture in a first area thereof, wherein, at least in an area of said edge, a roughness depth of said X-ray aperture in one wavelength range between 10 nm and 1 µm is smaller than 100 nm;
    a sample position onto which the X-ray beam, which is delimited by said at least one X-ray aperture, is directed, wherein said at least one X-ray aperture, is disposed at a separation from said sample position; and
    an X-ray detector for detecting X-ray radiation emanating from said sample position.

2. The X-ray analysis apparatus of claim 1, wherein said pinhole has a round or circular cross-section at least in said area of said edge and of said first area.

3. The X-ray analysis apparatus of claim 1, wherein said first area is designed like a truncated cone and has an opening angle α of between 5° and 60°.

4. The X-ray analysis apparatus of claim 1, wherein, starting from said edge, said pinhole widens like a funnel at a second area in a direction towards an inlet opening of said X-ray aperture.

5. The X-ray analysis apparatus of claim 1, wherein said edge is formed at a front side of said X-ray aperture, wherein said edge delimits an inlet opening of said X-ray aperture.

6. The X-ray analysis apparatus of claim 1, wherein an edge sharpness of said edge of said X-ray aperture has an edge radius<5 µm.

7. The X-ray analysis apparatus of claim 1, wherein said single crystal aperture body is connected or glued to an absorption structure, a material of said absorption structure absorbing X-ray radiation to a greater extent than a material of said single crystal aperture body, wherein said absorption structure is recessed with respect to said edge in a direction transverse to a direction of propagation of said X-ray beam which is delimited by said at least one X-ray aperture.

8. An X-ray analysis apparatus comprising:
    an X-ray source from which an X-ray beam is emitted;
    at least one X-ray aperture which delimits said X-ray beam emitted by said X-ray source, said at least one X-ray aperture having a single crystal aperture body with a through pinhole, wherein said single crystal aperture body consists of one single piece of monocrystalline material, said single crystal aperture body forming a continuous circumferential edge which delimits said X-ray beam and starting from which said pinhole widens like a funnel in a direction of an outlet opening of said X-ray aperture in a first area thereof;
    a sample position onto which the X-ray beam, which is delimited by said at least one X-ray aperture, is directed, wherein said at least one X-ray aperture, is disposed at a separation from said sample position;
    an X-ray detector for detecting X-ray radiation emanating from said sample position; and
    a cover structure to which said single crystal aperture body is connected or glued, wherein a material of said cover structure absorbs X-ray radiation to a lesser extent than a material of said aperture body, said cover structure covering an inlet opening and/or said outlet opening of said X-ray aperture or said pinhole is closed by said cover structure in a gas-tight or vacuum-tight fashion.

9. The X-ray analysis apparatus of claim 1, wherein the X-ray analysis apparatus comprises two X-ray apertures which are disposed at a separation from said sample position, each X-ray aperture comprising a single crystal aperture body with a through pinhole, wherein said single crystal aperture bodies each form a circumferential continuous edge that delimits said X-ray beam and starting from which said pinhole of a respective aperture body widens like a funnel in said first area towards an outlet opening of a respective said X-ray aperture.

10. The X-ray analysis apparatus of claim 1, wherein the X-ray analysis apparatus is designed as a small angle X-ray scattering measuring arrangement, as a single crystal X-ray scattering measuring arrangement or comprises a primary beam stop.

11. The X-ray analysis apparatus of claim 1, wherein the X-ray analysis apparatus is designed as a µ-XRD measuring arrangement.

12. A method for producing an X-ray aperture, the method comprising the steps of:
    a) introducing a through pinhole into a single crystal aperture body such that the single crystal aperture body forms a continuous circumferential edge for delimiting an X-ray beam, wherein, in a first area, the pinhole widens from that edge like a funnel in a direction towards an outlet opening, said single crystal aperture body consisting of one single piece of monocrystalline material; and
    b) removing, using ion beam etching, material from a surface of the aperture body, at least in an area of the edge and of the first area, wherein, at least in an area of the edge and of the first area, the pinhole in step a) is produced having round or circular cross-section and an ion beam with circular cross-section and Gaussian distributed intensity is used in step b), an intensity maximum of which is on a symmetry axis of a beam-defining cross-sectional area of the pinhole of the single crystal aperture body.

13. The method of claim 12, wherein electric discharge machining and/or cold laser ablation are used for introducing the pinhole in step a).

14. The method of claim 12, wherein, in step b), an opening facing away from an ion source, an inlet opening or the outlet opening of the X-ray aperture is not covered.

15. The method of claim 12, wherein the pinhole is introduced into the single crystal aperture body in step a) in such a fashion that the pinhole widens like a funnel starting from the edge in a second area towards an inlet opening of the X-ray aperture and that, in step b), material is also removed from a surface of the aperture body in the second area by ion beam etching.

16. A method for post-processing an X-ray aperture, the X-ray aperture having an aperture body forming an edge for delimiting an X-ray beam, wherein the aperture body consists of one single piece of monocrystalline material, the method comprising the steps of:
  a) using the X-ray aperture in an X-ray analysis apparatus; and
  b) removing, using ion beam etching and following step a), material from a surface of the aperture body, at least in an area of the edge.

\* \* \* \* \*